(12) United States Patent
Ogiso et al.

(10) Patent No.: US 7,094,516 B2
(45) Date of Patent: Aug. 22, 2006

(54) BENZOBISAZOLE COMPOUND AND OPTICAL RECORDING MEDIUM CONTAINING THE COMPOUND

(75) Inventors: Akira Ogiso, Sodegaura (JP); Shinobu Inoue, Sodegaura (JP); Hisashi Tsukahara, Sodegaura (JP); Taizo Nishimoto, Sodegaura (JP); Tsutami Misawa, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 41 days.

(21) Appl. No.: 10/169,197

(22) PCT Filed: Jan. 5, 2001

(86) PCT No.: PCT/JP01/00015

§ 371 (c)(1),
(2), (4) Date: Jun. 28, 2002

(87) PCT Pub. No.: WO01/49508

PCT Pub. Date: Jul. 12, 2001

(65) Prior Publication Data

US 2003/0091931 A1    May 15, 2003

(30) Foreign Application Priority Data

Jan. 7, 2000    (JP) .............................. 2000-001823

(51) Int. Cl.
*G11B 7/24* (2006.01)
*C07D 498/02* (2006.01)

(52) U.S. Cl. ................ 430/270.14; 430/945; 428/64.8; 369/288; 548/218

(58) Field of Classification Search ........... 430/270.14; 369/288; 548/150, 151, 218, 219, 220; 428/64.8
See application file for complete search history.

(56) References Cited

U.S. PATENT DOCUMENTS 2,807,622 A * 9/1957 Kern et al. .................. 548/218

(Continued)

FOREIGN PATENT DOCUMENTS

GB    2170505    * 8/1986

(Continued)

OTHER PUBLICATIONS

Machine translation of JP 11-116579.*

(Continued)

*Primary Examiner*—Martin Angebrannt
(74) *Attorney, Agent, or Firm*—Buchanan Ingersoll PC

(57) ABSTRACT

An optical recording medium having an organic dye layer as a recording layer on a substrate, wherein at least one benzobisazole-based compound represented by a general formula (1) is contained in the recording layer:

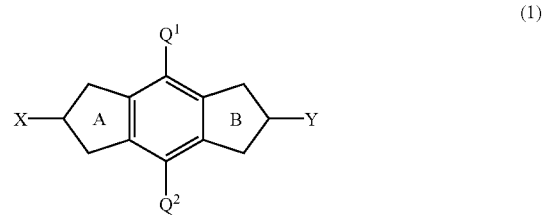

(1)

(wherein substituents X and Y each independently represent an aryl group or a heteroaryl group, rings A and B each independently represent an oxazole ring or a thiazole ring, and $Q^1$ and $Q^2$ each independently represent a hydrogen atom, a halogen atom or an alkyl group, with a proviso that, aryl group(s) or heteroaryl group(s) represented by the substituents X and Y each independently may be substituted by a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy or heterocyclic ring group).

5 Claims, 1 Drawing Sheet

U.S. PATENT DOCUMENTS

| | | | | |
|---|---|---|---|---|
| 2,807,662 A | * | 9/1957 | Mattingly | 348/707 |
| 3,336,328 A | * | 8/1967 | Bock | 548/106 |
| 3,501,293 A | * | 3/1970 | Clecak et al. | 430/77 |
| 4,065,462 A | * | 12/1977 | Frey et al. | 548/108 |
| 4,412,231 A | * | 10/1983 | Namba et al. | 346/135.1 |
| 5,075,147 A | * | 12/1991 | Usami et al. | 428/64.7 |
| 6,445,676 B1 | * | 9/2002 | Fujii et al. | 369/281 |

FOREIGN PATENT DOCUMENTS

| | | | |
|---|---|---|---|
| JP | 63-256624 | * | 10/1988 |
| JP | 02-289621 | * | 11/1990 |
| JP | 10-340786 A | | 12/1998 |
| JP | 11-116579 A | | 4/1999 |
| JP | 2000-158818 A | | 6/2000 |

OTHER PUBLICATIONS

Machine translation of JP 10-340486.*

* cited by examiner

BENZOBISAZOLE COMPOUND AND OPTICAL RECORDING MEDIUM CONTAINING THE COMPOUND

TECHNICAL FIELD

The present invention relates to a benzobisazole-based compound which is useful as a dye, pigment, photoelectric function material and recording/memory material, particularly as a recording dye for a high-capacity recordable optical recording medium which can be written information therein and read therefrom by means of a blue laser beam. Further, the present invention relates to an optical recording medium containing the benzobisazole-based compound as a recording material, particularly a recordable optical recording medium which can be written information therein and read therefrom by means of a blue laser beam.

BACKGROUND ART

A CD-R (CD-Recordable) is widely used as a recordable optical recording medium that is adapted to specifications of a compact disk (to be abbreviated as "CD" hereinafter). A recording capacity of the CD-R is about 680 MB. Along with a dramatic increase in an amount of information, demand for an information-recording medium with higher density and higher capacity has been increasing.

Use of laser beams for recording and reproducing which have short wavelengths can make a beam spot small, thereby making high-density optical recording possible. Lately, development of a short-wavelength semiconductor laser to be used in an optical disk system has been proceeding, and red semiconductor lasers for wavelengths of 680 nm, 660 nm, 650 nm and 635 nm are actually currently used (for example, refer to page 65 of Nikkei Electronics No. 592 published on Oct. 11, 1993). A DVD in which over two hours of motion pictures are digital-recorded by use of these semiconductor lasers has actually been used. Since the DVD is a playback-only medium, development of a recordable optical recording medium (DVD-R) corresponding to the capacity of the DVD is also under way.

In addition, development of a blue semiconductor laser for wavelengths ranging from 400 to 500 nm which makes ultra high density recording possible has been rapidly proceeding (for example, refer to page 117 of Nikkei Electronics No. 708 published on Jan. 26, 1998), and development of a recordable optical recording medium corresponding to the blue semiconductor laser is also under way.

In forming a pit by irradiating a recording layer of a recordable optical recording medium with a laser beam so as to cause a physical change and/or a chemical change in the recording layer, an optical constant and decomposition behavior of a compound are important factors for forming good pits. When the compound is not easily decomposed, sensitivity lowers, while when the compound is fiercely decomposed or susceptible to changes, influences between pits and in a radial direction become large, thereby making it difficult to form a reliable pit. When data is to be recorded on a conventional CD-R medium by use of a blue semiconductor laser wavelength, a refractive index of its recording layer is low and an extinction coefficient of the recording layer is also not an appropriate value, so that high recording properties cannot be attained. For this reason, as a compound used in the recording layer, a compound having appropriate optical properties and decomposition behavior against a blue semiconductor laser must be selected. As currently known examples of an organic dye compound for recording with a blue semiconductor laser, polyene-based dye compounds described in Japanese Patent Application Laid-Open Nos. 78576/1992 and 89279/1992, a styryl-based dye compound described in Japanese Patent Application Laid-Open No. 34489/1999, an indigoid-based dye compound described in Japanese Patent Application Laid-Open No. 78239/1999, a cyanoethene-based dye compound described in Japanese Patent Application Laid-Open No. 105423/1999 and a squarylium-based dye compound described in Japanese Patent Application Laid-Open No. 110815/1999 have been proposed in addition to cyanine-based dye compounds described in Japanese Patent Application Laid-Open Nos. 74690/1992 and 40161/1994 and porphyrin-based dye compounds described in Japanese Patent Application Laid-Open Nos. 304256/1995, 304257/1995, 127174/1996, 101953/1999 and 144312/1999.

Further, a variety of optical recording media having an improved layer structure such as an optical recording medium described in Japanese Patent Application Laid-Open No. 53758/1999 which comprises a recording layer comprised essentially of a porphyrin dye or a cyanine dye as an organic dye for forming the recording layer and a metal reflecting layer composed essentially of silver and an optical recording medium described in Japanese Patent Application Laid-Open No. 203729/1999 which makes recording over two wavelength ranges possible by having a blue sensitive dye layer containing a cyanine dye which is sensitive to a blue laser as well as a red sensitive dye layer or infrared sensitive dye layer have also been proposed.

Lately, a blue-violet semiconductor laser for wavelengths ranging from 400 to 410 nm has been developed, thereby making possible ultra high density optical recording of 15 to 30 GB capacity. Thus, development of a recordable optical recording medium which is the most suitable for the wavelength laser has been increasingly active (for example, refer to page 33 of Nikkei Electronics No. 736 published on Feb. 8, 1999, page 28 of Nikkei Electronics No. 741 published on Apr. 19, 1999, page 19 of Nikkei Electronics No. 748 published on Jul. 26, 1999, and page 117 of Nikkei Electronics No. 751 published on Sep. 6, 1999). However, it is a current situation that the aforementioned optical recording media for a blue semiconductor laser are not adapted to a laser beam having a wavelength of 400 to 410 nm sufficiently. That is, the present inventors have found that the aforementioned media using organic dyes have such a problem that signals recorded on the media may not be always able to be read satisfactorily since a carrier to noise ratio (C/N) is not always a good value. It has been an urgent necessity to solve the problem and develop an optical recording medium which makes possible high density recording/reproducing using a laser beam having a wavelength of 400 to 410 nm.

DISCLOSURE OF THE INVENTION

The present inventors have made studies on a recording material suited for a recordable optical recording medium. As a result, they have found the following two points:

(1) To write data in a high-capacity recordable optical recording medium and read data from the medium, a laser beam having a wavelength of 350 to 500 nm is used. Therefore, it is important to control an extinction coefficient, refractive index and reflectivity of a recording material in the vicinity of the wavelength of the laser.

(2) As described above, development of a high-capacity recordable optical recording medium using the laser has been accelerated. Particularly, development of a dye having high durability and good high-speed recording properties has been desired. Nevertheless, satisfactory characteristics are not yet attained for the aforementioned dye compounds as a recording medium which makes it possible to write and read data by use of a laser beam belonging to a blue wavelength range. Therefore, it still has room for improvements. Further, one advantageous characteristic in production of a medium by a coating method such as a spin coat method by which a recording film can be formed easily is to have high solubility in a coating solvent. Attention must also be paid to this point.

An object of the present invention is to invent a dye compound which is the most suitable for recording and reproduction of information by means of light and provide an optical medium which makes possible excellent optical recording and reproduction. Another object of the present invention is to provide an optical recording medium which makes possible good recording and reproduction using a blue semiconductor laser beam, particularly a laser beam whose wavelength is selected from a wavelength range of 400 to 410 nm and which has a recording layer suitable for ultra high density recording.

The present inventors have made intensive studies to solve the above problems. As a result, they have found a benzobisazole-based compound useful as a dye, pigment, photoelectric function material and recording material, particularly as a recording dye for a high-capacity recordable optical recording medium which data can be written in and read from by means of a blue laser beam and have completed the present invention based on the finding. In addition, they have also found an excellent optical recording medium which makes possible good recording and reproduction using a laser beam selected from oscillation wavelengths of 400 to 500 nm due to presence of a recording layer comprising the benzobisazole-based compound and have completed the present invention based on the finding.

That is, the present invention is concerned with:

(1) an optical recording medium having a recording layer on a substrate wherein at least one benzobisazole-based compound is selected and contained in the recording layer, and an optical recording medium having an organic dye layer as a recording layer on a substrate wherein at least one benzobisazole-based compound is contained in the organic dye, (2) the optical recording medium of the above (1) which makes possible recording and reproduction using a laser beam to be selected from wavelengths of preferably 300 to 500 nm, more preferably 400 to 500 nm, particularly preferably 400 to 410 nm, (3) an optical recording medium using a benzobisazole-based compound represented by a general formula (1):

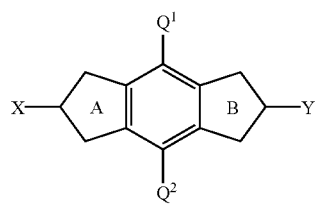

(1)

(wherein substituents X and Y each independently represent an aryl group or a heteroaryl group, rings A and B each independently represent an oxazole ring or a thiazole ring, and $Q^1$ and $Q^2$ each independently represent a hydrogen atom, a halogen atom or an alkyl group, with a proviso that, aryl group(s) or heteroaryl group(s) represented by the substituents X and Y each independently may be substituted by a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy or heterocyclic ring group), (4) the optical recording medium of (3) wherein the compound represented by the above general formula (1) is a compound represented by the following general formula (2):

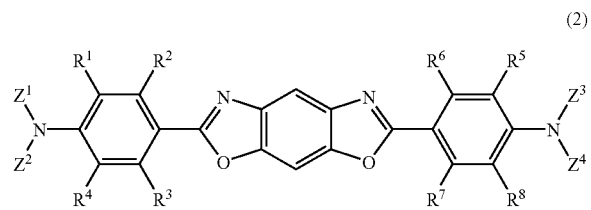

(2)

(wherein $R^1$, $R^2$, $R^3$, $R^4$, $R^5$, $R^6$, $R^7$ and $R^8$ each independently represent a hydrogen atom, a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl or acyloxy group, $Z^1$, $Z^2$, $Z^3$ and $Z^4$ each independently represent a hydrogen atom or a substituted or unsubstituted alkyl, aralkyl, aryl or alkenyl group, and substituents represented by $R^1$ to $R^8$ and $Z^1$ to $Z^4$ each may be joined to adjacent substituents via linking groups to form rings), (5) the optical recording medium of (3) wherein the compound represented by the above general formula (1) is a compound represented by the following general formula (3):

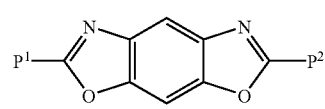

(3)

(wherein $P^1$ and $P^2$ each independently represent a substituted or unsubstituted naphthyl group, with the proviso that, in the case of a substituted naphthyl group, a substituent is selected from the group consisting of halogen atoms, a hydroxyl group, an amino group and substituted or unsubstituted alkyl, alkoxy, aralkyloxy, aryloxy, alkenyloxy, alkylthio, aralkylthio, arylthio, alkenylthio, mono-substituted amino, di-substituted amino and acyloxy groups)

(6) a benzobisazole-based compound represented by a general formula (1a):

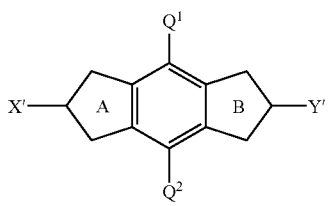

(1a)

(wherein substituents X' and Y' each independently represent an aryl group or a heteroaryl group, and rings A and B and $Q^1$ and $Q^2$ are the same as the rings A and B and $Q^1$ and $Q^2$ in the formula (1), with the proviso that, aryl group(s) or heteroaryl group(s) represented by the substituents X' and Y' each independently are substituted by a substituent selected from a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy or heterocyclic ring group, and at least one substituent represents a di-substituted amino group having three or more carbon atoms or an alkoxy group having 1 to 3 oxygen atoms in a carbon chain), (7) the benzobisazole-based compound of (6) which is represented by the following general formula (2a):

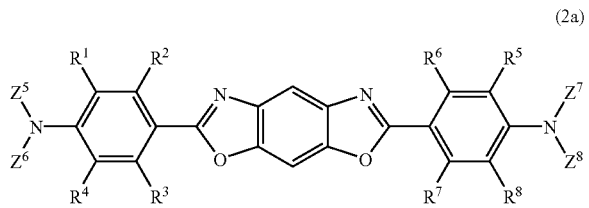

(2a)

(wherein $R^1$, $R^2$, $R^3$, $R^4$, $R^5$, $R^6$, $R^7$ and $R^8$ are the same as the $R^1$, $R^2$, $R^3$, $R^4$, $R^5$, $R^6$, $R^7$ and $R^8$ in the formula (2), and $Z^5$, $Z^6$, $Z^7$ and $Z^8$ each independently represent a substituted or unsubstituted alkyl, aralkyl, aryl or alkenyl group, with the proviso that, at least one of substituents represented by $Z^5$ to $Z^8$ represents an alkyl group having 4 to 10 carbon atoms or an aralkyl group having 7 to 10 carbon atoms), (8) the benzobisazole-based compound of (6) which is represented by the following general formula (3a):

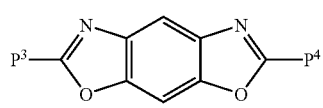

(3a)

(wherein $P^3$ and $P^4$ each independently represent a substituted or unsubstituted naphthyl group, with the proviso that, in the case of a substituted naphthyl group, a substituent is selected from the group consisting of halogen atoms, a hydroxyl group, an amino group and substituted or unsubstituted alkyl, alkoxy, aralkyloxy, aryloxy, alkenyloxy, alkylthio, aralkylthio, arylthio, alkenylthio, mono-substituted amino, di-substituted amino and acyloxy groups, at least one of $P^3$ and $P^4$ is a substituted naphthyl group, and at least one of the substituents represents an alkoxy group having one to three oxygen atoms in a carbon chain).

BEST MODE FOR CARRYING OUT THE INVENTION

The present invention relates to an optical recording medium which contains a benzobisazole-based compound in a recording layer of the optical recording medium. More specifically, the present invention relates to a novel optical recording medium which makes possible recording and reproduction using a laser beam selected from wavelengths of preferably 300 to 500 nm, more preferably 400 to 500 nm, particularly preferably 400 to 410 nm. Further, the present invention relates to a novel benzobisazole-based compound.

An optical recording medium according to the present invention refers to an optical recording medium which data can be recorded in and reproduced from. However, hereinafter, a description will be given with reference to, as an appropriate example, an optical recording medium of the present invention which has a recording layer and a reflective layer on a substrate.

Figure 1:
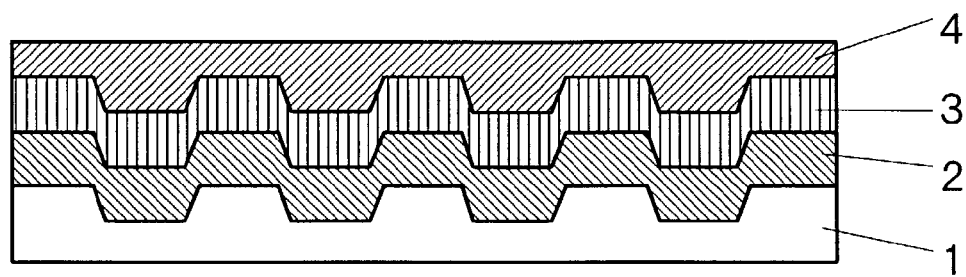
FIG. 1 is a cross-sectional structural diagram showing an example of a layer structure of an optical recording medium according to the present invention.
Figure 2:
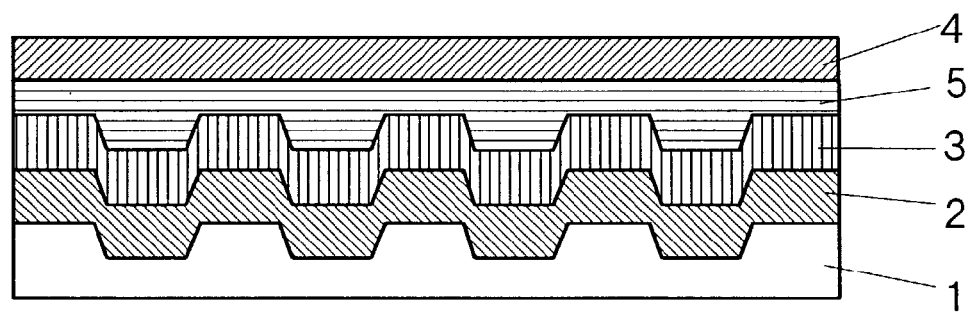
FIG. 2 is a cross-sectional structural diagram showing an example of a layer structure of an optical recording medium according to the present invention.
Figure 3:
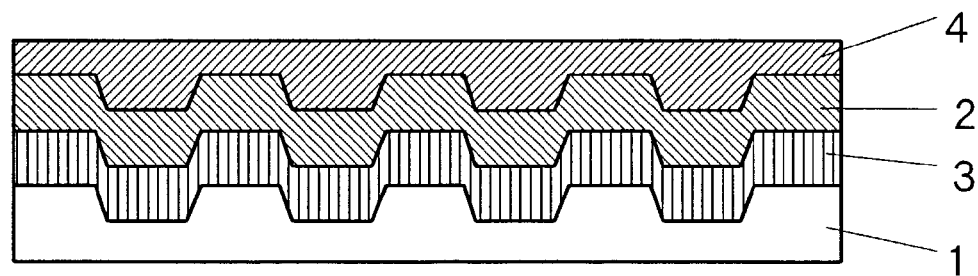
FIG. 3 is a cross-sectional structural diagram showing an example of a layer structure of an optical recording medium according to the present invention.

The optical recording medium according to the present invention has, for example, a four-layer structure as shown in FIG. 1 in which a substrate 1, a recording layer 2, a reflective layer 3 and a protective layer 4 are built up in order. Alternatively, the optical recording medium has a laminated structure as shown in FIG. 2. That is, a medium shown in FIG. 2 has a structure in that a recording layer 2 is formed on a substrate 1, a reflective layer 3 is formed in close contact with the recording layer 2, and a protective layer 4 is laminated on the reflective layer 3 via an adhesive layer 5. However, another layer may exist under or on the recording layer 2, and another layer may exist on the reflective layer 3. Further, as shown in FIG. 3, the optical recording medium may have a structure that the substrate 1, the reflective layer 3, the recording layer 2 and the protective layer 4 are built up in the order presented and recording and reproduction are performed on the protective layer. Alternatively, it may have a medium structure as disclosed in Japanese Patent Application Laid-Open No. 326435/1998 in which a thickness of a light transmitting layer is defined by a laser light source wavelength λ of a reproduction system and a numerical aperture, N.A., of an objective lens. As for the compound of the formula (1) in the present invention, it can be used in an optical recording medium as described in Japanese Patent Application Laid-Open No. 203729/1999 which has two or more recording layers as required.

A material of the substrate is basically one which is transparent at wavelengths of light for recording and light for reproduction. For example, a polymer material such as a polycarbonate resin, a vinyl chloride resin, an acrylic resin, e.g., polymethyl methacrylate, a polystyrene resin or an epoxy resin or an inorganic material such as glass is used. These substrate materials may be molded into a disk-shaped substrate by a method such as an injection molding method. Guide grooves and/or pits may be formed on the surface of the substrate as required. Although such guide grooves and pits are desirably formed at the time of molding the substrate, they may be provided by use of an ultraviolet curable resin layer on the substrate.

Generally, when used as an optical disk, the substrate may be a disk having a thickness of about 1.2 mm and a diameter of about 80 to 120 mm and may have a hole having a diameter of about 15 mm in the center.

In the present invention, a recording layer is formed on a substrate. The recording layer in the present invention contains at least one benzobisazole-based compound. Further, the recording layer can be subjected to recording and reproduction using a recording laser and reproduction laser whose wavelengths are selected from a range of 300 to 500 nm. In particular, the optical recording medium of the present invention is an optical recording medium which can show good signal properties for a recording laser and reproduction laser whose wavelengths are selected from a range of preferably 400 to 500 nm, more preferably 400 to 410 nm.

As for the compound represented by the general formula (1) set forth in the present specification, its absorption wavelength can be arbitrarily selected according to selection of a substituent. Therefore, it is an extremely useful organic dye which can satisfy an optical constant required for the recording layer over the above laser beam wavelengths.

Hereinafter, specific examples of the compound represented by the general formula (1) which is contained in the recording layer of the present invention will be set forth in detail.

In the formula (1), substituents X and Y each independently represent a substituted or unsubstituted aryl or heteroaryl group. As these groups, groups which are suitable for forming a layer on a substrate made of a polymer material such as a polycarbonate, acryl, epoxy or polyolefin resin or an inorganic material such as glass and which have good processability can be selected and used.

Illustrative examples of substituents in aryl and heteroaryl groups represented by the substituents X and Y in the formula (1) include a halogen atom, a hydroxyl group, a cyano group, an amino group and substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy or heterocyclic ring groups.

Illustrative examples of a halogen atom substituted into the aryl and heteroaryl groups represented by the substituents X and Y in the formula (1) include halogen atoms such as a fluorine atom, a chlorine atom, a bromine atom and an iodine atom.

Illustrative examples of a substituted or unsubstituted alkyl group substituted into the aryl and heteroaryl groups represented by the substituents X and Y in the formula (1) include a linear, branched or cyclic unsubstituted alkyl group; an alkyl group substituted by a substituent selected from a group of substituents including a halogen atom, a hydroxyl group, a cyano group, an alkoxy group, an acyl group, an acyloxy group, an alkoxycarbonyl group, an aryloxycarbonyl group, an aralkyloxycarbonyl group, an alkenyloxycarbonyl group, an alkoxycarbonyloxy group, a dialkylamino group, an acylamino group, an alkylsulfoneamino group, an alkylsulfonyl group, an arylsulfonyl group, a heterocyclic ring group and the like.

Illustrative examples of the substituted or unsubstituted linear, branched or cyclic alkyl group include an unsubstituted alkyl group having 1 to 15 carbon atoms such as methyl group, ethyl group, n-propyl group, iso-propyl group, n-butyl group, iso-butyl group, sec-butyl group, t-butyl group, n-pentyl group, iso-pentyl group, 2-methylbutyl group, 1-methylbutyl group, neopentyl group, 1,2-dimethylpropyl group, 1,1-dimethylpropyl group, cyclopentyl group, n-hexyl group, 4-methylpentyl group, 3-methylpentyl group, 2-methylpentyl group, 1-methylpentyl group, 3,3-dimethylbutyl group, 2,3-dimethylbutyl group, 1,3-dimethylbutyl group, 2,2-dimethylbutyl group, 1,2-dimethylbutyl group, 1,1-dimethylbutyl group, 3-ethylbutyl group, 2-ethylbutyl group, 1-ethylbutyl group, 1,2,2-trimethylbutyl group, 1,1,2-trimethylbutyl group, 1-ethyl-2-methylpropyl group, cyclohexyl group, n-heptyl group, 2-methylhexyl group, 3-methylhexyl group, 4-methylhexyl group, 5-methylhexyl group, 2,4-dimethylpentyl group, n-octyl group, 2-ethylhexyl group, 2,5-dimethylhexyl group, 2,5,5-trimethylpentyl group, 2,4-dimethylhexyl group, 2,2,4-trimethylpentyl group, 3,5,5-trimethylhexyl group, n-nonyl group, n-decyl group, 4-ethyloctyl group, 4-ethyl-4,5-methylhexyl group, n-undecyl group, n-dodecyl group, 1,3,5,7-tetraethyloctyl group, 4-butyloctyl group, 6,6-diethyloctyl group, n-tridecyl group, 6-methyl-4-butyloctyl group, n-tetradecyl group, n-pentadecyl group, 3,5-dimethylheptyl group, 2,6-dimethylheptyl group, 2,4-dimethylheptyl group, 2,2,5,5-tetramethylhexyl group, 1-cyclopentyl-2,2-dimethylpropyl group and 1-cyclohexyl-2,2-dimethylpropyl group;

an alkyl group having 1 to 10 carbon atoms and substituted by a halogen atom such as chloromethyl group, chloroethyl group, bromoethyl group, iodoethyl group, dichloromethyl group, fluoromethyl group, trifluoromethyl group, pentafluoroethyl group, 2,2,2-trifluoroethyl group, 2,2,2-trichloroethyl group, 1,1,1,3,3,3-hexafluoro-2-propyl group, nonafluorobutyl group and perfluorodecyl group;

an alkyl group having 1 to 10 carbon atoms and substituted by a hydroxy group such as hydroxymethyl group, 2-hydroxyethyl group, 4-hydroxybutyl group, 2-hydroxy-3-methoxypropyl group, 2-hydroxy-3-chloropropyl group, 2-hydroxy-3-ethoxypropyl group, 3-butoxy-2-hydroxypropyl group, 2-hydroxy-3-cyclohexyloxypropyl group, 2-hydroxypropyl group, 2-hydroxybutyl group and 4-hydroxydecaryl group;

an alkyl group having 2 to 10 carbon atoms and substituted by hydroxyalkoxy group such as hydroxymethoxymethyl group, hydroxyethoxyethyl group, 2-(2'-hydroxy-1'-methylethoxy)-1-methylethyl group, 2-(3'-fluoro-2'-hydroxypropoxy)ethyl group, 2-(3'-chloro-2'-hydroxypropoxy)ethyl group and hydroxybutoxycyclohexyl group;

an alkyl group having 3 to 10 carbon atoms and substituted by a hydroxyalkoxyalkoxy group such as hydroxymethoxymethoxymethyl group, hydroxyethoxyethoxyethyl group, [2-(2'-hydroxy-1'-methylethoxy)-1-methylethoxy]ethoxyethyl group, [2-(2'-fluoro-1'-hydroxyethoxy)-1-methylethoxy]ethoxyethyl group and [2-(2'-chloro-1'-hydroxyethoxy)-1-methylethoxy]ethoxyethyl group;

an alkyl group having 2 to 10 carbon atoms and substituted by a cyano group such as cyanomethyl group, 2-cyanoethyl group, 4-cyanobutyl group, 2-cyano-3-methoxypropyl group, 2-cyano-3-chloropropyl group, 2-cyano-3-ethoxypropyl group, 3-butoxy-2-cyanopropyl group, 2-cyano-3-cyclohexylpropyl group, 2-cyanopropyl group and 2-cyanobutyl group;

an alkyl group having 2 to 15 carbon atoms and substituted by an alkoxy group such as methoxymethyl group, ethoxymethyl group, propoxymethyl group, butoxymethyl group, methoxyethyl group, ethoxyethyl group, propoxyethyl group, butoxyethyl group, n-hexyloxyethyl group, (4-methylpentoxy)ethyl group, (1,3-dimethylbutoxy)ethyl group, (2-ethylhexyloxy)ethyl group, n-octyloxyethyl group, (3,5,5-trimethylhexyloxy)ethyl group, (2-methyl-1-iso-propylpropoxy)ethyl group, (3-methyl-1-iso-propylbutyloxy)ethyl group, 2-ethoxy-1-methylethyl group, 3-methoxybutyl group, (3,3,3-trifluoropropoxy)ethyl group and (3,3,3-trichloropropoxy)ethyl group;

an alkyl group having 3 to 15 carbon atoms and substituted by an alkoxyalkoxy group such as methoxymethoxyethyl group, methoxyethoxyethyl group, an ethoxyethoxyethyl group, propoxyethoxyethyl group, butoxyethoxyethyl group, cyclohexyloxyethoxyethyl group, decalyloxypropoxyethoxy group, (1,2-dimethylpropoxy)ethoxyethyl group, (3-methyl-1-iso-butylbutoxy)ethoxyethyl group, (2-methoxy-1-methylethoxy)ethyl group, (2-butoxy-1-methylethoxy)ethyl group, 2-(2'-ethoxy-1'-methylethoxy)-1-methylethyl group, a (3,3,3-trifluoropropoxy)ethoxyethyl group and a (3,3,3-trichloropropoxy)ethoxyethyl group;

an alkyl group having 4 to 15 carbon atoms and substituted by an alkoxyalkoxyalkoxy group such as methoxymethoxymethoxymethyl group, methoxyethoxyethoxyethyl group, ethoxyethoxyethoxyethyl group, butoxyethoxyethoxyethyl group, cyclohexyloxy group, propoxypropoxypropoxy group, (2,2,2-trifluoroethoxy)ethoxyethoxyethyl group and (2,2,2-trichloroethoxy)ethoxyethoxyethyl group;

an alkyl group having 2 to 10 carbon atoms and substituted by an acyl group such as formylmethyl group, 2-oxobutyl group, 3-oxobutyl group, 4-oxobutyl group, 2,6-dioxocyclohexan-1-yl group and 2-oxo-5-t-butylcyclohexan-1-yl group;

an alkyl group having 2 to 15 carbon atoms and substituted by an acyloxy group such as formyloxymethyl group, acetoxyethyl group, propionyloxyethyl group, butanoyloxyethyl group, valeryloxyethyl group, (2-ethylhexanoyloxy)ethyl group, (3,5,5-trimethylhexanoyloxy)ethyl group, (3,5,5-trimethylhexanoyloxy)hexyl group, (3-fluorobutyryloxy)ethyl group and (3-chlorobutyryloxy)ethyl group;

an alkyl group having 3 to 15 carbon atoms and substituted by an acyloxyalkoxy group such as formyloxymethoxymethyl group, acetoxyethoxyethyl group, propionyloxyethoxyethyl group, valeryloxyethoxyethyl group, (2-ethylhexanoyloxy)ethoxyethyl group, (3,5,5-trimethylhexanoyloxy)butoxyethyl group, (3,5,5-trimethylhexanoyloxy)ethoxyethyl group, (2-fluoropropionyloxy)ethoxyethyl group and (2-chloropropionyloxy)ethoxyethyl group;

an alkyl group having 5 to 15 carbon atoms and substituted by an acyloxyalkoxyalkoxy group such as acetoxymethoxymethoxymethyl group, acetoxyethoxyethoxyethyl group, propionyloxyethoxyethoxyethyl group, valeryloxyethoxyethoxyethyl group, (2-ethylhexanoyloxy)ethoxyethoxyethyl group, (3,5,5-trimethylhexanoyloxy)ethoxyethoxyethyl group, (2-fluoropropionyloxy)ethoxyethoxyethyl group and (2-chloropropionyloxy)ethoxyethoxyethyl group;

an alkyl group having 3 to 15 carbon atoms and substituted by an alkoxycarbonyl group such as methoxycarbonylmethyl group, ethoxycarbonylmethyl group, butoxycarbonylmethyl group, methoxycarbonylethyl group, ethoxycarbonylethyl group, butoxycarbonylethyl group, (p-ethylcyclohexyloxycarbonyl)cyclohexyl group, (2,2,3,3-tetrafluoropropoxycarbonyl)methyl group and (2,2,3,3-tetrachloropropoxycarbonyl)methyl group;

an alkyl group having 8 to 15 carbon atoms and substituted by an aryloxycarbonyl group such as phenoxycarbonylmethyl group, phenoxycarbonylethyl group, (4-t-butylphenoxycarbonyl)ethyl group, naphthyloxycarbonylmethyl group and biphenyloxycarbonylethyl group;

an alkyl group having 9 to 15 carbon atoms and substituted by an aralkyloxycarbonyl group such as benzyloxycarbonylmethyl group, benzyloxycarbonylethyl group, phenethyloxycarbonylmethyl group and (4-cyclohexyloxybenzyloxycarbonyl)methyl group;

an alkyl group having 4 to 10 carbon atoms and substituted by an alkenyloxycarbonyl group such as vinyloxycarbonylmethyl group, vinyloxycarbonylethyl group, an allyloxycarbonylmethyl group and octenoxycarbonylmethyl group;

an alkyl group having 3 to 15 carbon atoms and substituted by an alkoxycarbonyloxy group such as methoxycarbonyloxymethyl group, methoxycarbonyloxyethyl group, ethoxycarbonyloxyethyl group, butoxycarbonyloxyethyl group, (2,2,2-trifluoroethoxy)carbonyloxyethyl group and (2,2,2-trichloroethoxy)carbonyloxyethyl group;

an alkyl group having 4 to 15 carbon atoms and substituted by an alkoxyalkoxycarbonyloxy group such as methoxymethoxycarbonyloxymethyl group, methoxyethoxycarbonyloxyethyl group, ethoxyethoxycarbonyloxyethyl group, butoxyethoxycarbonyloxyethyl group, (2,2,2-trifluoroethoxy)ethoxycarbonyloxyethyl and (2,2,2-trichloroethoxy)ethoxycarbonyloxyethyl;

an alkyl group having 3 to 20 carbon atoms and substituted by a dialkylamino group such as dimethylaminomethyl group, diethylaminomethyl group, di-n-butylaminomethyl group, di-n-hexylaminomethyl group, di-n-octylaminomethyl group, di-n-decylaminomethyl group, N-isoamyl-N-methylaminomethyl group, piperidinomethyl group, di(methoxymethyl)aminomethyl group, di(methoxyethyl)aminomethyl group, di(ethoxymethyl)aminomethyl group, di(ethoxyethyl)aminomethyl group, di(propoxyethyl)aminomethyl group, di(butoxyethyl)aminomethyl group, bis(2-cyclohexyloxyethyl)aminomethyl group, dimethylaminoethyl group, diethylaminoethyl group, di-n-butylaminoethyl group, di-n-hexylaminoethyl group, di-n-octylaminoethyl group, di-n-decylaminoethyl group, N-isoamyl-N-methylaminoethyl group, piperidinoethyl group, di(methoxymethyl)aminoethyl group, di(methoxyethyl)aminoethyl group, di(ethoxymethyl)aminoethyl group, di(ethoxyethyl)aminoethyl group, di(propoxyethyl)aminoethyl group, di(butoxyethyl)aminoethyl group, bis(2-cyclohexyloxyethyl)aminoethyl group, dimethylaminopropyl group, diethylaminopropyl group, di-n-butylaminopropyl group, di-n-hexylaminopropyl group, di-n-octylaminopropyl group, di-n-decylaminopropyl group, N-isoamyl-N-methylaminopropyl group, piperidinopropyl group, di(methoxymethyl)aminopropyl group, di(methoxyethyl)aminopropyl group, di(ethoxymethyl)aminopropyl group, di(ethoxyethyl)aminopropyl group, di(propoxyethyl)aminopropyl group, di(butoxyethyl)aminopropyl group, bis(2-cyclohexyloxyethyl)aminopropyl group, dimethylaminobutyl group, diethylaminobutyl group, di-n-butylaminobutyl group, di-n-hexylaminobutyl group, di-n-octylaminobutyl group, di-n-decylaminobutyl group, N-isoamyl-N-methylaminobutyl group, piperidinobutyl group, di(methoxymethyl)aminobutyl group, di(methoxyethyl)aminobutyl group, di(ethoxyethyl)aminobutyl group, di(ethoxyethyl)aminobutyl group, di(propoxyethyl)aminobutyl group, di(butoxyethyl)aminobutyl group and bis(2-cyclohexyloxyethyl)aminobutyl group;

an alkyl group having 3 to 10 carbon atoms and substituted by an acylamino group such as acetylaminomethyl group, acetylaminoethyl group, propionylaminoethyl group, butanoylaminoethyl group, cyclohexanecarbonylaminoethyl group, p-methylcyclohexanecarbonylaminoethyl group and succiniminoethyl group;

an alkyl group having 2 to 10 carbon atoms and substituted by an alkylsulfoneamino group such as methylsulfoneaminomethyl group, methylsulfoneaminoethyl group, ethylsulfoneaminoethyl group, propylsulfoneaminoethyl group and an octylsulfoneaminoethyl group;

an alkyl group having 2 to 10 carbon atoms and substituted by an alkylsulfonyl group such as methylsulfonylmethyl group, ethylsulfonylmethyl group, butylsulfonylmethyl group, methylsulfonylethyl group, ethylsulfonylethyl group, butylsulfonylethyl group, 2-ethylhexylsulfonylethyl group, (2,2,3,3-tetrafluoropropyl)sulfonylmethyl group and (2,2,3,3-tetrachloropropyl)sulfonylmethyl group;

an alkyl group having 7 to 12 carbon atoms and substituted by an arylsulfonyl group such as benzenesulfonylmethyl group, benzenesulfonylethyl group, benzenesulfonylpropyl group, benzenesulfonylbutyl group, toluenesulfonylmethyl group, toluenesulfonylethyl group, toluenesulfonylpropyl group, toluenesulfonylbutyl group, xylenesulfonylmethyl group, xylenesulfonylethyl group, xylenesulfonylpropyl group and xylenesulfonylbutyl group; and an alkyl group having 2 to 13 carbon atoms and substituted by a heterocyclic ring group such as thiadiazolinomethyl group, pyrrolinomethyl group, pyrrolidinomethyl group, pyrazolidinomethyl group, imidazolidinomethyl group, an oxazolyl group, triazolinomethyl group, morpholinomethyl group, indolinomethyl group, benzimidazolinomethyl group and carbazolinomethyl group.

Illustrative examples of a substituted or unsubstituted aralkyl group substituted into the aryl and heteroaryl groups represented by the substituents X and Y in the formula (1) include aralkyl groups having the same substituents as those in the alkyl groups enumerated above. Preferable examples thereof include an aralkyl group having 7 to 15 carbon atoms such as benzyl group, nitrobenzyl group, cyanobenzyl group, hydroxybenzyl group, methylbenzyl group, trifluoromethylbenzyl group, naphthylmethyl group, nitronaphthylmethyl group, cyanonaphthylmethyl group, hydroxynaphthylmethyl group, methylnaphthylmethyl group, trifluoromethylnaphthylmethyl group and fluoren-9-ylethyl group.

Illustrative examples of a substituted or unsubstituted aryl group substituted into the aryl and heteroaryl groups represented by the substituents X and Y in the formula (1) include aryl groups having the same substituents as those in the alkyl groups enumerated above. Preferable examples thereof include an aryl group having 6 to 15 carbon atoms such as phenyl group, nitrophenyl group, cyanophenyl group, hydroxyphenyl group, methylphenyl group, trifluoromethylphenyl group, naphthyl group, nitronaphthyl group, cyanonaphthyl group, hydroxynaphthyl group, methylnaphthyl group, trifluoromethylnaphthyl group, methoxycarbonylphenyl group, 4-(5'-methylbenzoxazol-2'-yl)phenyl group and dibutylaminocarbonylphenyl group.

Illustrative examples of a substituted or unsubstituted alkenyl group substituted into the aryl and heteroaryl groups represented by the substituents X and Y in the formula (1) include alkenyl groups having the same substituents as those in the alkyl groups enumerated above. Preferable examples thereof include an alkenyl group having 2 to 10 carbon atoms such as vinyl group, propenyl group, 1-butenyl group, iso-butenyl group, 1-pentenyl group, 2-pentenyl group, 2-methyl-1-butenyl group, 3-methyl-1-butenyl group, 2-methyl-2-butenyl group, 2,2-dicyanovinyl group, 2-cyano-2-methylcarboxylvinyl group, 2-cyano-2-methylsulfonevinyl group, styryl group and 4-phenyl-2-butenyl group.

Illustrative examples of a substituted or unsubstituted alkoxy group substituted into the aryl and heteroaryl groups represented by the substituents X and Y in the formula (1) include an unsubstituted linear, branched or cyclic alkoxy group having 1 to 15 carbon atoms such as methoxy group, ethoxy group, n-propoxy group, isopropoxy group, n-butoxy group, isobutoxy group, t-butoxy group, sec-butoxy group, n-pentyloxy group, isopentyloxy group, t-pentyloxy group, sec-pentyloxy group, cyclopentyloxy group, n-hexyloxy group, 1-methylpentyloxy group, 2-methylpentyloxy group, 3-methylpentyloxy group, 4-methylpentyloxy group, 1,1-dimethylbutoxy group, 1,2-dimethylbutoxy group, 1,3-dimethylbutoxy group, 2,3-dimethylbutoxy group, 1,1,2-trimethylpropoxy group, 1,2,2-trimethylpropoxy group, 1-ethylbutoxy group, 2-ethylbutoxy group, 1-ethyl-2-methylpropoxy group, cyclohexyloxy group, methylcyclopentyloxy group, n-heptyloxy group, 1-methylhexyloxy group, 2-methylhexyloxy group, 3-methylhexyloxy group, 4-methylhexyloxy group, 5-methylhexyloxy group, 1,1-dimethylpentyloxy group, 1,2-dimethylpentyloxy group, 1,3-dimethylpentyloxy group, 1,4-dimethylpentyloxy group, 2,2-dimethylpentyloxy group, 2,3-dimethylpentyloxy group, 2,4-dimethylpentyloxy group, 3,3-dimethylpentyloxy group, 3,4-dimethylpentyloxy group, 1-ethylpentyloxy group, 2-ethylpentyloxy group, 3-ethylpentyloxy group, 1,1,2-trimethylbutoxy group, 1,1,3-trimethylbutoxy group, 1,2,3-trimethylbutoxy group, 1,2,2-trimethylbutoxy group, 1,3,3-trimethylbutoxy group, 2,3,3-trimethylbutoxy group, 1-ethyl-1-methylbutoxy group, 1-ethyl-2-methylbutoxy group, 1-ethyl-3-methylbutoxy group, 2-ethyl-1-methylbutoxy group, 2-ethyl-3-methylbutoxy group, 1-n-propylbutoxy group, 1-isopropylbutoxy group, 1-isopropyl-2-methylpropoxy group, methylcyclohexyloxy group, n-octyloxy group, 1-methylheptyloxy group, 2-methylheptyloxy group, 3-methylheptyloxy group, 4-methylheptyloxy group, 5-methylheptyloxy group, 6-methylheptyloxy group, 1,1-dimethylhexyloxy group, 1,2-dimethylhexyloxy group, 1,3-dimethylhexyloxy group, 1,4-dimethylhexyloxy group, 1,5-dimethylhexyloxy group, 2,2-dimethylhexyloxy group, 2,3-dimethylhexyloxy group, 2,4-dimethylhexyloxy group, 2,5-dimethylhexyloxy group, 3,3-dimethylhexyloxy group, 3,4-dimethylhexyloxy group, 3,5-dimethylhexyloxy group, 4,4-dimethylhexyloxy group, 4,5-dimethylhexyloxy group, 1-ethylhexyloxy group, 2-ethylhexyloxy group, 3-ethylhexyloxy group, 4-ethylhexyloxy group, 1-n-propylpentyloxy group, 2-n-propylpentyloxy group, 1-isopropylpentyloxy group, 2-isopropylpentyloxy group, 1-ethyl-1-methylpentyloxy group, 1-ethyl-2-methylpentyloxy group, 1-ethyl-3-methylpentyloxy group, 1-ethyl-4-methylpentyloxy group, 2-ethyl-1-methylpentyloxy group, 2-ethyl-2-methylpentyloxy group, 2-ethyl-3-methylpentyloxy group, 2-ethyl-4-methylpentyloxy group, 3-ethyl-1-methylpentyloxy group, 3-ethyl-2-methylpentyloxy group, 3-ethyl-3-methylpentyloxy group, 3-ethyl-4-methylpentyloxy group, 1,1,2-trimethylpentyloxy group, 1,1,3-trimethylpentyloxy group, 1,1,4-trimethylpentyloxy group, 1,2,2-trimethylpentyloxy group, 1,2,3-trimethylpentyloxy group, 1,2,4-trimethylpentyloxy group, 1,3,4-trimethylpentyloxy group, 2,2,3-trimethylpentyloxy group, 2,2,4-trimethylpentyloxy group, 2,3,4-trimethylpentyloxy group, 1,3,3-trimethylpentyloxy group, 2,3,3-trimethylpentyloxy group, 3,3,4-trimethylpentyloxy group, 1,4,4-trimethylpentyloxy group, 2,4,4-trimethylpentyloxy group, 3,4,4-trimethylpentyloxy group, 1-n-butylbutoxy group, 1-isobutylbutoxy group, 1-sec-butylbutoxy group, 1-t-butylbutoxy group, 2-t-butylbutoxy group, 1-n-propyl-1-methylbutoxy group, 1-n-propyl-2-methylbutoxy group, 1-n-propyl-3-methylbutoxy group, 1-isopropyl-1-methylbutoxy group, 1-isopropyl-2-methylbutoxy group, 1-isopropyl-3-methylbutoxy group, 1,1-diethylbutoxy group, 1,2-diethylbutoxy group, 1-ethyl-1,2-dimethylbutoxy group, 1-ethyl-1,3-dimethylbutoxy group, 1-ethyl-2,3-dimethylbutoxy group, 2-ethyl-1,1-dimethylbutoxy group, 2-ethyl-1,2-dimethylbutoxy group, 2-ethyl-1,3-dimethylbutoxy group, 2-ethyl-2,3-dimethylbutoxy group, 1,1,3,3-tetramethylbutoxy group, 1,2-dimethylcyclohexyloxy group, 1,3-dimethylcyclohexyloxy group, 1,4-dimethylcyclohexyloxy group, ethylcyclohexyloxy group, n-nonyloxy group, 3,5,5-trimethylhexyloxy group, n-decyloxy group, n-undecyloxy group, n-dodecyloxy group, 1-adamantyloxy group and n-pentadecyloxy group;

an alkoxy group having 2 to 15 carbon atoms and substituted by an alkoxy group such as methoxymethoxy group, methoxyethoxy group, ethoxyethoxy group, n-propoxyethoxy group, isopropoxyethoxy group, n-butoxyethoxy group, isobutoxyethoxy group, t-butoxyethoxy group, sec-butoxyethoxy group, n-pentyloxyethoxy group, isopentyloxyethoxy group, t-pentyloxyethoxy group, sec-pentyloxyethoxy group, cyclopentyloxyethoxy group, n-hexyloxyethoxy group, ethylcyclohexyloxyethoxy group, n-nonyloxyethoxy group, (3,5,5-trimethylhexyloxy)ethoxy group, (3,5,5-trimethylhexyloxy)butoxy group, n-decyloxyethoxy group, n-undecyloxyethoxy group, n-dodecyloxyethoxy group, 3-methoxypropoxy group, 3-ethoxypropoxy group, 3-(n-propoxy)propoxy group, 2-isopropoxypropoxy group, 2-methoxybutoxy group, 2-ethoxybutoxy group, 2-(n-propoxy)butoxy group, 4-isopropoxybutoxy group, decaryloxyethoxy group and adamantyloxyethoxy group;

a linear, branched or cyclic alkoxy group having 3 to 15 carbon atoms and substituted by an alkoxyalkoxy group such as methoxymethoxymethoxy group, ethoxymethoxymethoxy group, propoxymethoxymethoxy group, butoxymethoxymethoxy group, methoxyethoxymethoxy group, ethoxyethoxymethoxy group, propoxyethoxymethoxy group, butoxyethoxymethoxy group, methoxypropoxymethoxy group, ethoxypropoxymethoxy group, propoxypropoxymethoxy group, butoxypropoxymethoxy group, methoxybutoxymethoxy group, ethoxybutoxymethoxy group, propoxybutoxymethoxy group, butoxybutoxymethoxy group, methoxymethoxyethoxy group, ethoxymethoxyethoxy group, propoxymethoxyethoxy group, butoxymethoxyethoxy group, methoxyethoxyethoxy group, ethoxyethoxyethoxy group, propoxyethoxyethoxy group, butoxyethoxyethoxy group, methoxypropoxyethoxy group, ethoxypropoxyethoxy group, propoxypropoxyethoxy group, butoxypropoxyethoxy group, methoxybutoxyethoxy group, ethoxybutoxyethoxy group, propoxybutoxyethoxy group, butoxybutoxyethoxy group, methoxymethoxypropoxy group, ethoxymethoxypropoxy group, propoxymethoxypropoxy group, butoxymethoxypropoxy group, methoxyethoxypropoxy group, ethoxyethoxypropoxy group, propoxyethoxypropoxy group, butoxyethoxypropoxy group, methoxypropoxypropoxy group, ethoxypropoxypropoxy group, propoxypropoxypropoxy group, butoxypropoxypropoxy group, methoxybutoxypropoxy group, ethoxybutoxypropoxy group, propoxybutoxypropoxy group, butoxybutoxypropoxy group, methoxymethoxybutoxy group, ethoxymethoxybutoxy group, propoxymethoxybutoxy group, butoxymethoxybutoxy group, methoxyethoxybutoxy group, ethoxyethoxybutoxy group, propoxyethoxybutoxy group, butoxyethoxybutoxy group, methoxypropoxybutoxy group, ethoxypropoxybutoxy group, propoxypropoxybutoxy group, butoxypropoxybutoxy group, methoxybutoxybutoxy group, ethoxybutoxybutoxy group, propoxybutoxybutoxy group, butoxybutoxybutoxy group, (4-ethylcyclohexyloxy)ethoxyethoxy group, (2-ethyl-1-hexyloxy)ethoxypropoxy group and [4-(3,5,5-trimethylhexyloxy)butoxy]ethoxy group;

an alkoxy group having 3 to 10 carbon atoms and substituted by an alkoxycarbonyl group such as methoxycarbonylmethoxy group, ethoxycarbonylmethoxy group, n-propoxycarbonylmethoxy group, isopropoxycarbonylmethoxy group and (4'-ethylcyclohexyloxy)carbonylmethoxy group;

an alkoxy group having 3 to 10 carbon atoms and substituted by an acyl group such as acetylmethoxy group, ethylcarbonylmethoxy group, octylcarbonylmethoxy group and phenacyloxy group;

an alkoxy group having 3 to 10 carbon atoms and substituted by an acyloxy group such as acetyloxymethoxy group, acetyloxyethoxy group, acetyloxyhexyloxy group and butanoyloxycyclohexyloxy group;

an alkoxy group having 2 to 10 carbon atoms and substituted by an alkylamino group such as methylaminomethoxy group, 2-methylaminoethoxy group, 2-(2-methylaminoethoxy)ethoxy group, 4-methylaminobutoxy group, 1-methylaminopropane-2-yloxy group, 3-methylaminopropoxy group, 2-methylamino-2-methylpropoxy group, 2-ethylaminoethoxy group, 2-(2-ethylaminoethoxy)ethoxy group, 3-ethylaminopropoxy group, 1-ethylaminopropoxy group, 2-isopropylaminoethoxy group, 2-(n-butylamino)ethoxy group, 3-(n-hexylamino)propoxy group and 4-(cyclohexylamino)butyloxy group;

an alkoxy group having 3 to 10 carbon atoms and substituted by an alkylaminoalkoxy group such as methylaminomethoxymethoxy group, methylaminoethoxyethoxy group, methylaminoethoxypropoxy group, ethylaminoethoxypropoxy group and 4-(2'-isobutylaminopropoxy)butoxy group;

an alkoxy group having 3 to 15 carbon atoms and substituted by a dialkylamino group such as dimethylaminomethoxy group, 2-dimethylaminoethoxy group, 2-(2-dimethylaminoethoxy)ethoxy group, 4-dimethylaminobutoxy group, 1-dimethylaminopropane-2-yloxy group, 3-dimethylaminopropoxy group, 2-dimethylamino-2-methylpropoxy group, 2-diethylaminoethoxy group, 2-(2-diethylaminoethoxy)ethoxy group, 3-diethylaminopropoxy group, 1-diethylaminopropoxy group, 2-diisopropylaminoethoxy group, 2-(di-n-butylamino)ethoxy group, 2-piperidylethoxy group and 3-(di-n-hexylamino)propoxy group;

an alkoxy group having 4 to 15 carbon atoms and substituted by a dialkylaminoalkoxy group such as dimethylaminomethoxymethoxy group, dimethylaminoethoxyethoxy group, dimethylaminoethoxypropoxy group, diethylaminoethoxypropoxy group and 4-(2'-diisobutylaminopropoxy)butoxy group; and an alkoxy group having 2 to 15 carbon atoms and substituted by an alkylthio group such as methylthiomethoxy group, 2-methylthioethoxy group, 2-ethylthioethoxy group, 2-n-propylthioethoxy group, 2-isopropylthioethoxy group, 2-n-butylthioethoxy group, 2-isobutylthioethoxy group and (3,5,5-trimethylhexylthio)hexyloxy group. Preferable examples thereof include an alkoxy group having 1 to 10 carbon atoms such as methoxy group, ethoxy group, n-propoxy group, iso-propoxy group, n-butoxy group, iso-butoxy group, sec-butoxy group, t-butoxy group, n-pentoxy group, iso-pentoxy group, neopentoxy group, 2-methylbutoxy group, 2-ethylhexyloxy group, 3,5,5-trimethylhexyloxy group, decaryloxy group, methoxyethoxy group, ethoxyethoxy group, methoxyethoxyethoxy group and ethoxyethoxyethoxy group.

Illustrative examples of a substituted or unsubstituted aralkyloxy group substituted into the aryl and heteroaryl groups represented by the substituents X and Y in the formula (1) include aralkyloxy groups having the same substituents as those in the alkyl groups enumerated above. Preferable examples thereof include an aralkyloxy group having 7 to 15 carbon atoms such as benzyloxy group, nitrobenzyloxy group, cyanobenzyloxy group, hydroxybenzyloxy group, methylbenzyloxy group, trifluoromethylbenzyloxy group, naphthylmethoxy group, nitronaphthylmethoxy group, cyanonaphthylmethoxy group, hydroxynaphthylmethoxy group, methylnaphthylmethoxy group, trifluoromethylnaphthylmethoxy group and fluoren-9-ylethoxy group.

Illustrative examples of a substituted or unsubstituted aryloxy group substituted into the aryl and heteroaryl groups represented by the substituents X and Y in the formula (1) include aryloxy groups having the same substituents as those in the alkyl groups enumerated above. Preferable examples thereof include an aryloxy group having 6 to 10 carbon atoms such as phenoxy group, 2-methylphenoxy group, 4-methylphenoxy group, 4-t-butylphenoxy group, 2-methoxyphenoxy group, 4-iso-propylphenoxy group and naphthoxy group.

Illustrative examples of a substituted or unsubstituted alkenyloxy group substituted into the aryl and heteroaryl groups represented by the substituents X and Y in the formula (1) include alkenyloxy groups having the same substituents as those in the alkyl groups enumerated above. Preferable examples thereof include an alkenyloxy group having 2 to 10 carbon atoms such as vinyloxy group, propenyloxy group, 1-butenyloxy group, iso-butenyloxy group, 1-pentenyloxy group, 2-pentenyloxy group, 2-methyl-1-butenyloxy group, 3-methyl-1-butenyloxy group, 2-methyl-2-butenyloxy group, 2,2-dicyanovinyloxy group, 2-cyano-2-methylcarboxylvinyloxy group, 2-cyano-2-methylsulfonevinyloxy group, styryloxy group, 4-phenyl-2-butenyloxy group and cinnamylalkoxy group.

Illustrative examples of a substituted or unsubstituted alkylthio group substituted into the aryl and heteroaryl groups represented by the substituents X and Y in the formula (1) include alkylthio groups having the same substituents as those in the alkyl groups enumerated above. Preferable examples thereof include an alkylthio group having 1 to 10 carbon atoms such as methylthio group, ethylthio group, n-propylthio group, iso-propylthio group, n-butylthio group, iso-butylthio group, sec-butylthio group, t-butylthio group, n-pentylthio group, iso-pentylthio group, neopentylthio group, 2-methylbutylthio group, methylcarboxylethylthio group, 2-ethylhexylthio group, 3,5,5-trimethylhexylthio group and decarylthio group.

Illustrative examples of a substituted or unsubstituted aralkylthio group substituted into the aryl and heteroaryl groups represented by the substituents X and Y in the formula (1) include aralkylthio groups having the same substituents as those in the alkyl groups enumerated above.

Preferable examples thereof include an aralkylthio group having 7 to 12 carbon atoms such as benzylthio group, nitrobenzylthio group, cyanobenzylthio group, hydroxybenzylthio group, methylbenzylthio group, trifluoromethylbenzylthio group, naphthylmethylthio group, nitronaphthylmethylthio group, cyanonaphthylmethylthio group, hydroxynaphthylmethylthio group, methylnaphthylmethylthio group, trifluoromethylnaphthylmethylthio group and fluoren-9-ylethylthio group.

Illustrative examples of a substituted or unsubstituted arylthio group substituted into the aryl and heteroaryl groups represented by the substituents X and Y in the formula (1) include arylthio groups having the same substituents as those in the alkyl groups enumerated above. Preferable examples thereof include an arylthio group having 6 to 10 carbon atoms such as phenylthio group, 4-methylphenylthio group, 2-methoxyphenylthio group, 4-t-butylphenylthio group and naphthylthio group.

Illustrative examples of a substituted or unsubstituted alkenylthio group substituted into the aryl and heteroaryl groups represented by the substituents X and Y in the formula (1) include alkenylthio groups having the same substituents as those in the alkyl groups enumerated above. Preferable examples thereof include an alkenylthio group having 2 to 10 carbon atoms such as vinylthio group, allylthio group, butenylthio group, hexanedienylthio group, styrylthio group, cyclohexenylthio group and decenylthio group.

Illustrative examples of a substituted or unsubstituted mono-substituted amino group substituted into the aryl and heteroaryl groups represented by the substituents X and Y in the formula (1) include mono-substituted amino groups having the same substituents as those in the alkyl groups enumerated above. Preferable examples of such mono-substituted amino groups include a monoalkylamino group having 1 to 10 carbon atoms such as methylamino group, ethylamino group, propylamino group, butylamino group, pentylamino group, hexylamino group, heptylamino group, octylamino group, (2-ethylhexyl)amino group, cyclohexylamino group, (3,5,5-trimethylhexyl)amino group, nonylamino group and decylamino group;

a monoaralkylamino group having 7 to 10 carbon atoms such as benzylamino group, phenethylamino group, (3-phenylpropyl)amino group, (4-ethylbenzyl)amino group, (4-isopropylbenzyl)amino group, (4-methylbenzyl)amino group, (4-allylbenzyl)amino group, [4-(2-cyanoethyl)benzyl]amino group and [4-(2-acetoxyethyl)benzyl]amino group;

a monoarylamino group having 6 to 10 carbon atoms such as anilino group, naphthylamino group, toluidino group, xylidino group, ethylanilino group, isopropylanilino group, methoxyanilino group, ethoxyanilino group, chloroanilino group, acetylanilino group, methoxycarbonylanilino group, ethoxycarbonylanilino group, propoxycarbonylanilino group, 4-methylanilino group, 4-ethylanilino group and 2-methyltoluidino group;

a monoalkenylamino group having 2 to 10 carbon atoms such as vinylamino group, allylamino group, butenylamino group, pentenylamino group, hexenylamino group, cyclohexenylamino group, octadienylamino group and adamantenylamino group; and an acylamino group having 1 to 15 carbon atoms such as formylamino group, methylcarbonylamino group, ethylcarbonylamino group, n-propylcarbonylamino group, iso-propylcarbonylamino group, n-butylcarbonylamino group, iso-butylcarbonylamino group, sec-butylcarbonylamino group, t-butylcarbonylamino group, n-pentylcarbonylamino group, iso-pentylcarbonylamino group, neopentylcarbonylamino group, 2-methylbutylcarbonylamino group, benzoylamino group, methylbenzoylamino group, ethylbenzoylamino group, tolylcarbonylamino group, propylbenzoylamino group, 4-t-butylbenzoylamino group, nitrobenzylcarbonylamino group, 3-butoxy-2-naphthoylamino group and cinnamoylamino group.

Illustrative examples of a substituted or unsubstituted di-substituted amino group substituted into the aryl and heteroaryl groups represented by the substituents X and Y in the formula (1) include di-substituted amino groups having the same substituents as those in the alkyl groups enumerated above. Preferable examples of such di-substituted amino groups include a dialkylamino group having 2 to 16 carbon atoms such as dimethylamino group, diethylamino group, methylethylamino group, dipropylamino group, dibutylamino group, di-n-hexylamino group, dicyclohexylamino group, dioctylamino group, bis(methoxyethyl)amino group, bis(ethoxyethyl)amino group, bis(propoxyethyl)amino group, bis(butoxyethyl)amino group, di(acetyloxyethyl)amino group, di(hydroxyethyl)amino group, N-ethyl-N-(2-cyanoethyl)amino group and di(propionyloxyethyl)amino group; diaralkylamino group having 14 to 20 carbon atoms such as dibenzylamino group, diphenethylamino group, bis(4-ethylbenzyl)amino group and bis(4-isopropylbenzyl)amino group;

a diarylamino group having 12 to 14 carbon atoms such as diphenylamino group, ditolylamino group and N-phenyl-N-tolylamino group;

a dialkenylamino group having 4 to 12 carbon atoms such as divinylamino group, diallylamino group, dibutenylamino group, dipentenylamino group, dihexenylamino group and N-vinyl-N-allylamino group;

a di-substituted amino group having 3 to 10 carbon atoms and selected from substituted or unsubstituted alkyl, aralkyl, aryl and alkenyl groups such as N-phenyl-N-allylamino group, N-(2-acetyloxyethyl)-N-ethylamino group, N-tolyl-N-methylamino group, N-vinyl-N-methylamino group and N-benzyl-N-allylamino group; and a diacylamino group having 2 to 30 carbon atoms such as diformylamino group, di(methylcarbonyl)amino group, di(ethylcarbonyl)amino group, di(n-propylcarbonyl)amino group, di(iso-propylcarbonyl)amino group, di(n-butylcarbonyl)amino group, di(iso-butylcarbonyl)amino group, di(sec-butylcarbonyl)amino group, di(t-butylcarbonyl)amino group, di(n-pentylcarbonyl)amino group, di(iso-pentylcarbonyl)amino group, di(neopentylcarbonyl)amino group, di(2-methylbutylcarbonyl)amino group, di(benzoyl)amino group, di(methylbenzoyl)amino group, di(ethylbenzoyl)amino group, di(tolylcarbonyl)amino group, di(propylbenzoyl)amino group, di(4-t-butylbenzoyl)amino group, di(nitrobenzylcarbonyl)amino group, di(3-butoxy-2-naphthoyl)amino group and di(cinnamoyl)amino group.

Illustrative examples of a substituted or unsubstituted acyl group substituted into the aryl and heteroaryl groups represented by the substituents X and Y in the formula (1) include acyl groups having the same substituents as those in the alkyl groups enumerated above. Preferable examples thereof include an acyl group having 1 to 15 carbon atoms such as formyl group, methylcarbonyl group, ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, iso-pentylcarbonyl group, neopentylcarbonyl group, 2-methylbutylcarbonyl group, benzoyl group, methylbenzoyl group, ethylbenzoyl group, tolylcarbonyl group, propylbenzoyl group, 4-t-butylbenzoyl group, nitrobenzylcarbonyl group, 3-butoxy-2-naphthoyl group and cinnamoyl group.

Illustrative examples of a substituted or unsubstituted alkoxycarbonyl group substituted into the aryl and heteroaryl groups represented by the substituents X and Y in the formula (1) include alkoxycarbonyl groups having the same substituents as those in the alkyl groups enumerated above. Preferable examples thereof include an alkoxycarbonyl group having 2 to 11 carbon atoms such as methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group, t-butoxycarbonyl group, n-pentoxycarbonyl group, iso-pentoxycarbonyl group, neopentoxycarbonyl group, 2-pentoxycarbonyl group, 2-ethylhexyloxycarbonyl group, 3,5,5-trimethylhexyloxycarbonyl group, decaryloxycarbonyl group, cyclohexyloxycarbonyl group, chloroethoxycarbonyl group, hydroxymethoxycarbonyl group and hydroxyethoxycarbonyl group;

an alkoxycarbonyl group having 3 to 11 carbon atoms and substituted by an alkoxy group such as methoxymethoxycarbonyl group, methoxyethoxycarbonyl group, an ethoxyethoxycarbonyl group, propoxyethoxycarbonyl group, butoxyethoxycarbonyl group, pentoxyethoxycarbonyl group, hexyloxyethoxycarbonyl group, butoxybutoxycarbonyl group, hexyloxybutoxycarbonyl group, hydroxymethoxymethoxycarbonyl group and hydroxyethoxyethoxycarbonyl group; and an alkoxycarbonyl group having 4 to 11 carbon atoms and substituted by an alkoxyalkoxy group such as methoxymethoxymethoxycarbonyl group, methoxyethoxyethoxycarbonyl group, ethoxyethoxyethoxycarbonyl group, propoxyethoxyethoxycarbonyl group, butoxyethoxyethoxycarbonyl group, pentoxyethoxyethoxycarbonyl group and hexyloxyethoxyethoxycarbonyl group.

Illustrative examples of a substituted or unsubstituted aralkyloxycarbonyl group substituted into the aryl and heteroaryl groups represented by the substituents X and Y in the formula (1) include aralkyloxycarbonyl groups having the same substituents as those in the alkyl groups enumerated above. Preferable examples thereof include an aralkyloxycarbonyl group having 8 to 16 carbon atoms such as benzyloxycarbonyl group, nitrobenzyloxycarbonyl group, cyanobenzyloxycarbonyl group, hydroxybenzyloxycarbonyl group, methylbenzyloxycarbonyl group, trifluoromethylbenzyloxycarbonyl group, naphthylmethoxycarbonyl group, nitronaphthylmethoxycarbonyl group, cyanonaphthylmethoxycarbonyl group, hydroxynaphthylmethoxycarbonyl group, methylnaphthylmethoxycarbonyl group, trifluoromethylnaphthylmethoxycarbonyl group and fluorene-9-ylethoxycarbonyl group.

Illustrative examples of a substituted or unsubstituted aryloxycarbonyl group substituted into the aryl and heteroaryl groups represented by the substituents X and Y in the formula (1) include aryloxycarbonyl groups having the same substituents as those in the alkyl groups enumerated above. Preferable examples thereof include an aryloxycarbonyl group having 7 to 11 carbon atoms such as phenoxycarbonyl group, 2-methylphenoxycarbonyl group, 4-methylphenoxycarbonyl group, 4-t-butylphenoxycarbonyl group, 2-methoxyphenoxycarbonyl group, 4-iso-propylphenoxycarbonyl group and naphthoxycarbonyl group.

Illustrative examples of a substituted or unsubstituted alkenyloxycarbonyl group substituted into the aryl and heteroaryl groups represented by the substituents X and Y in the formula (1) include alkenyloxycarbonyl groups having the same substituents as those in the alkyl groups enumerated above. Preferable examples thereof include an alkenyloxycarbonyl group having 3 to 11 carbon atoms such as vinyloxycarbonyl group, propenyloxycarbonyl group, 1-butenyloxycarbonyl group, iso-butenyloxycarbonyl group, 1-pentenyloxycarbonyl group, 2-pentenyloxycarbonyl group, 2-methyl-1-butenyloxycarbonyl group, 3-methyl-1-butenyloxycarbonyl group, 2-methyl-2-butenyloxycarbonyl group, 2,2-dicyanovinyloxycarbonyl group, 2-cyano-2-methylcarboxylvinyloxycarbonyl group, 2-cyano-2-methylsulfonevinyloxycarbonyl group, styryloxycarbonyl group and 4-phenyl-2-butenyloxycarbonyl group.

Illustrative examples of a substituted or unsubstituted mono-substituted aminocarbonyl group substituted into the aryl and heteroaryl groups represented by the substituents X and Y in the formula (1) include mono-substituted aminocarbonyl groups having the same substituents as those in the alkyl groups enumerated above. Preferable examples of such mono-substituted aminocarbonyl groups include a monoalkylaminocarbonyl group having 2 to 11 carbon atoms such as methylaminocarbonyl group, ethylaminocarbonyl group, propylaminocarbonyl group, butylaminocarbonyl group, pentylaminocarbonyl group, hexylaminocarbonyl group, heptylaminocarbonyl group, octylaminocarbonyl group, (2-ethylhexyl)aminocarbonyl group, cyclohexylaminocarbonyl group, (3,5,5-trimethylhexyl)aminocarbonyl group, nonylaminocarbonyl group and decylaminocarbonyl group;

a monoaralkylaminocarbonyl group having 8 to 11 carbon atoms such as benzylaminocarbonyl group, phenethylaminocarbonyl group, (3-phenylpropyl)aminocarbonyl group, (4-ethylbenzyl)aminocarbonyl group, (4-isopropylbenzyl)aminocarbonyl group, (4-methylbenzyl)aminocarbonyl group, (4-allylbenzyl)aminocarbonyl group, [4-(2-cyanoethyl)benzyl]aminocarbonyl group and [4-(2-acetoxyethyl)benzyl]aminocarbonyl group;

a monoarylaminocarbonyl group having 7 to 11 carbon atoms such as anilino group, naphthylaminocarbonyl group, toluidino group, xylidino group, ethylanilino group, isopropylanilino group, methoxyanilino group, ethoxyanilino group, chloroanilino group, acetylanilino group, methoxycarbonylanilino group, ethoxycarbonylanilino group, propoxycarbonylanilino group, 4-methylanilino group, 4-ethylanilino group and 2-methyltoluidino group; and a monoalkenylaminocarbonyl group having 3 to 11 carbon atoms such as vinylaminocarbonyl group, allylaminocarbonyl group, butenylaminocarbonyl group, pentenylaminocarbonyl group, hexenylaminocarbonyl group, cyclohexenylaminocarbonyl group, octadienylaminocarbonyl group, adamantenylaminocarbonyl group and methylvinylaminocarbonyl group.

Illustrative examples of a substituted or unsubstituted di-substituted aminocarbonyl group substituted into the aryl and heteroaryl groups represented by the substituents X and Y in the formula (1) include di-substituted aminocarbonyl groups having the same substituents as those in the alkyl groups enumerated above. Preferable examples of such di-substituted aminocarbonyl groups include a dialkylaminocarbonyl group having 3 to 17 carbon atoms such as dimethylaminocarbonyl group, diethylaminocarbonyl group, methylethylaminocarbonyl group, dipropylaminocarbonyl group, dibutylaminocarbonyl group, di-n-hexylaminocarbonyl group, dicyclohexylaminocarbonyl group, dioctylaminocarbonyl group, pyrrolidino group, piperidino group, morpholino group, bis(methoxyethyl)aminocarbonyl group, bis(ethoxyethyl)aminocarbonyl group, bis(propoxyethyl)aminocarbonyl group, bis(butoxyethyl)aminocarbonyl group, di(acetyloxyethyl)aminocarbonyl group, di(hydroxyethyl)aminocarbonyl group, N-ethyl-N-(2-cyanoethyl)aminocarbonyl group and di(propionyloxyethyl)aminocarbonyl group;

a diaralkylaminocarbonyl group having 15 to 21 carbon atoms such as dibenzylaminocarbonyl group, diphenethylaminocarbonyl group, bis(4-ethylbenzyl)aminocarbonyl group and bis(4-isopropylbenzyl)aminocarbonyl group;

a diarylaminocarbonyl group having 13 to 15 carbon atoms such as diphenylaminocarbonyl group, ditolylaminocarbonyl group and N-phenyl-N-tolylaminocarbonyl group;

a dialkenylaminocarbonyl group having 5 to 13 carbon atoms such as divinylaminocarbonyl group, diallylaminocarbonyl group, dibutenylaminocarbonyl group, dipentenylaminocarbonyl group, dihexenylaminocarbonyl group and N-vinyl-N-allylaminocarbonyl group; and a di-substituted aminocarbonyl group having 4 to 11 carbon atoms and selected from substituted or unsubstituted alkyl, aralkyl, aryl and alkenyl groups such as N-phenyl-N-allylaminocarbonyl group, N-(2-acetyloxyethyl)-N-ethylaminocarbonyl group, N-tolyl-N-methylaminocarbonyl group, N-vinyl-N-methylaminocarbonyl group and N-benzyl-N-allylaminocarbonyl group.

Illustrative examples of a substituted or unsubstituted acyloxy group substituted into the aryl and heteroaryl groups represented by the substituents X and Y in the formula (1) include acyloxy groups having the same substituents as those in the alkyl groups enumerated above. Preferable examples thereof include an acyloxy group having 2 to 16 carbon atoms such as formyloxy group, methylcarbonyloxy group, ethylcarbonyloxy group, n-propylcarbonyloxy group, iso-propylcarbonyloxy group, n-butylcarbonyloxy group, iso-butylcarbonyloxy group, sec-butylcarbonyloxy group, t-butylcarbonyloxy group, n-pentylcarbonyloxy group, iso-pentylcarbonyloxy group, neopentylcarbonyloxy group, 2-methylbutylcarbonyloxy group, benzoyloxy group, methylbenzoyloxy group, ethylbenzoyloxy group, tolylcarbonyloxy group, propylbenzoyloxy group, 4-t-butylbenzoyloxy group, nitrobenzylcarbonyloxy group, 3-butoxy-2-naphthoyloxy group and cinnamoyloxy group.

Illustrative examples of a substituted or unsubstituted heterocyclic ring group substituted into the aryl and heteroaryl groups represented by the substituents X and Y in the formula (1) include heterocyclic ring groups having the same substituents as those in the alkyl groups enumerated above. Preferable examples thereof include unsubstituted heterocyclic ring groups such as furanyl group, pyrrolyl group, 3-pyrrolino group, pyrrolidino group, 1,3-oxolanyl group, pyrazolyl group, 2-pyrazolynyl group, pyrazolydinyl group, imidazolyl group, oxazolyl group, thiazolyl group, 1,2,3-oxadiazolyl group, 1,2,3-triazolyl group, 1,2,4-triazolyl group, 1,3,4-thiadiazolyl group, 4H-pyranyl group, pyridinyl group, piperidinyl group, dioxanyl group, morpholinyl group, pyridazinyl group, pyrimidinyl group, pyrazinyl group, piperazinyl group, triazinyl group, benzofuranyl group, indolyl group, thionaphthenyl group, benzimidazolyl group, benzthiazolyl group, benzotriazole-2-yl group, benzotriazole-1-yl group, purinyl group, quinolinyl group, isoquinolinyl group, coumarinyl group, cinnolinyl group, quinoxalinyl group, dibenzofuranyl group, carbazolyl group, phenanthronilyl group, phenothiadinyl group, flavonyl group, phthalimide group and naphthylimide group; and heterocyclic ring groups substituted by the following substituents, i.e., halogen atoms such as fluorine atom, chlorine atom, bromine atom and iodine atom;

a cyano group;

alkyl groups such as methyl group, ethyl group, propyl group, butyl group, pentyl group, hexyl group, heptyl group, octyl group, decyl group, methoxymethyl group, ethoxyethyl group, ethoxyethyl group and trifluoromethyl group;

aralkyl groups such as a benzyl group and a phenethyl group;

aryl groups such as phenyl group, tolyl group, naphthyl group, xylyl group, mesyl group, chlorophenyl group and methoxyphenyl group; alkoxy groups such as methoxy group, ethoxy group, propoxy group, butoxy group, pentoxy group, hexyloxy group, heptyloxy group, octyloxy group, nonyloxy group, decyloxy group, 2-ethylhexyloxy group and 3,5,5-trimethylhexyloxy group;

aralkyloxy groups such as benzyloxy group and phenethyloxy group;

aryloxy groups such as phenoxy group, tolyloxy group, naphthoxy group, xylyloxy group, mesityloxy group, chlorophenoxy group and methoxyphenoxy group;

alkenyl groups such as vinyl group, allyl group, butenyl group, butadienyl group, pentenyl group and octenyl group;

alkenyloxy groups such as vinyloxy group, allyloxy group, butenyloxy group, butadienyloxy group, pentenyloxy group and octenyloxy group;

alkylthio groups such as methylthio group, ethylthio group, propylthio group, butylthio group, pentylthio group, hexylthio group, heptylthio group, octylthio group, decylthio group, methoxymethylthio group, ethoxyethylthio group, ethoxyethylthio group and trifluoromethylthio group;

aralkylthio groups such as benzylthio group and phenethylthio group; arylthio groups such as phenylthio group, tolylthio group, naphthylthio group, xylylthio group, mesylthio group, chlorophenylthio group and methoxyphenylthio group;

dialkylamino groups such as dimethylamino group, diethylamino group, dipropylamino group and dibutylamino group;

acyl groups such as acetyl group, propionyl group and butanoyl group;

alkoxycarbonyl groups such as methoxycarbonyl group and ethoxycarbonyl group;

aralkyloxycarbonyl groups such as benzyloxycarbonyl group and phenethyloxycarbonyl group; aryloxycarbonyl groups such as phenoxycarbonyl group, tolyloxycarbonyl group, naphthoxycarbonyl group, xylyloxycarbonyl group, mesyloxycarbonyl group, chlorophenoxycarbonyl group and methoxyphenoxycarbonyl group;

alkenyloxycarbonyl groups such as vinyloxycarbonyl group, allyloxycarbonyl group, butenyloxycarbonyl group, butadienyloxycarbonyl group, pentenyloxycarbonyl group and octenyloxycarbonyl group;

alkylaminocarbonyl groups such as monoalkylaminocarbonyl group having 2 to 10 carbon atoms, e.g., methylaminocarbonyl group, ethylaminocarbonyl group, propylaminocarbonyl group, butylaminocarbonyl group, pentylaminocarbonyl group, hexylaminocarbonyl group, heptylaminocarbonyl group, octylaminocarbonyl group, nonylaminocarbonyl group, 3,5,5-trimethylhexylaminocarbonyl group and 2-ethylhexylaminocarbonyl group; as well as dialkylaminocarbonyl groups having 3 to 20 carbon atoms, e.g., dimethylaminocarbonyl group, diethylaminocarbonyl group, dipropylaminocarbonyl group, dibutylaminocarbonyl group, dipentylaminocarbonyl group, dihexylaminocarbonyl group, diheptylaminocarbonyl group, dioctylaminocarbonyl group, piperidinocarbonyl group, morpholinocarbonyl group, 4-methylpiperadinocarbonyl group and 4-ethylpiperadinocarbonyl group; and heterocyclic ring groups such as furanyl group, pyrrolyl group, 3-pyrrolino group, pyrrolidino group, 1,3-oxolanyl group, pyrazolyl group, 2-pyrazolynyl group, pyrazolydinyl group, imidazolyl group, oxazolyl group, thiazolyl group, 1,2,3-oxadiazolyl group, 1,2,3-triazolyl group, 1,2,4-triazolyl group, 1,3,4-thiadiazolyl group, 4H-pyranyl group, pyridinyl group, piperidinyl group, dioxanyl group, morpholinyl group, pyridazinyl group, pyrimidinyl group, pyrazinyl group, piperazinyl group, triazinyl group, benzofuranyl group, indolyl group, thionaphthenyl group, benzimidazolyl group, benzothiazolyl group, purinyl group, quinolinyl group, isoquinolinyl group, coumarinyl group, cinnolinyl group, quinoxalinyl group, dibenzofuranyl group, carbazolyl group, phenanthronilyl group, phenothiadinyl group and flavonyl group.

The substituents X and Y in the general formula (1) are a substituted or unsubstituted aryl or heteroaryl group. The aryl group is preferably a phenyl group or a naphthyl group.

A specific example of a skeleton of a substituted or unsubstituted phenyl group suitable as the substituent X in a compound of the general formula (1) which is used in the present invention is a phenyl group represented by the following formula (4):

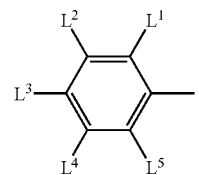

(4)

(wherein $L^1$, $L^2$, $L^3$, $L^4$ and $L^5$ represent the same groups as those linked to a phenyl group represented by the substituent X in the formula (1), i.e., a hydrogen atom, a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy or heterocyclic ring group).

Suitable substituents for $L^1$, $L^2$, $L^3$, $L^4$ and $L^5$ in the formula (4) are a substituted or unsubstituted amino group, preferably a substituted or unsubstituted amino group represented by a formula (5):

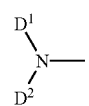

(5)

(wherein $D^1$ and $D^2$ each independently represent a hydrogen atom or a substituted or unsubstituted alkyl, aralkyl, aryl or alkenyl group), and in particular, more preferably a di-substituted amino group represented by a formula (6):

(6)

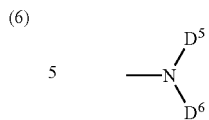
(8)

(wherein $D^3$ and $D^4$ each independently represent a substituted or unsubstituted alkyl, aralkyl, aryl or alkenyl group).

More preferable examples of substituents for $D^3$ and $D^4$ in the formula (6) include the alkyl groups having 4 to 10 carbon atoms and aralkyl groups having 7 to 10 carbon atoms which have been shown with respect to the above-exemplified alkyl and aralkyl groups to be substituted into the substituents X and Y in the general formula (1).

Further, $L^1$ to $L^5$ may be joined to adjacent substituents via linking groups to form an aliphatic condensed ring, an aromatic condensed ring or a heterocyclic condensed ring.

Illustrative examples of such condensed rings include an aliphatic condensed ring such as

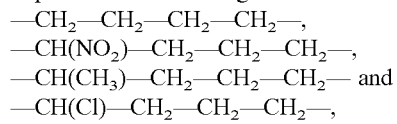

an aromatic condensed ring such as

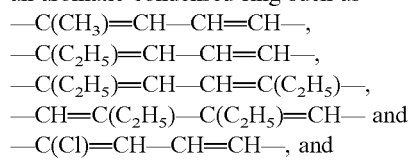

and a heterocyclic condensed ring group such as

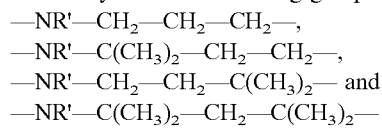

(wherein R' represents a hydrogen atom, an alkyl group, an aralkyl group, an aryl group, an alkenyl group or an alkylene group).

Meanwhile, a specific example of a skeleton of a substituted or unsubstituted phenyl group suitable as the substituent Y in the compound of the formula (1) is a phenyl group represented by a formula (7):

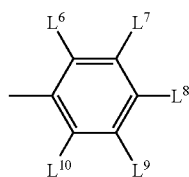
(7)

(wherein $L^6$, $L^7$, $L^8$, $L^9$ and $L^{10}$ are groups linked to a phenyl group represented by the substituent Y in the formula (1) and represent the same groups as those represented by $L^1$, $L^2$, $L^3$, $L^4$ and $L^5$).

Suitable substituents for $L^6$, $L^7$, $L^8$, $L^9$ and $L^{10}$ in the formula (7) are a substituted or unsubstituted amino group, preferably a substituted or unsubstituted amino group represented by a formula (8):

(wherein $D^5$ and $D^6$ each independently represent a hydrogen atom or a substituted or unsubstituted alkyl, aralkyl, aryl or alkenyl group), and in particular, more preferably a di-substituted amino group represented by a formula (9):

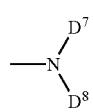
(9)

(wherein $D^7$ and $D^8$ each independently represent a substituted or unsubstituted alkyl, aralkyl, aryl or alkenyl group).

More preferable examples of substituents for $D^7$ and $D^8$ in the formula (9) include the alkyl groups having 4 to 10 carbon atoms and aralkyl groups having 7 to 10 carbon atoms which have been shown with respect to the above-exemplified alkyl and aralkyl groups to be substituted into the substituents X and Y in the general formula (1).

Further, $L^6$ to $L^{10}$ may be joined to adjacent substituents via linking groups to form an aliphatic condensed ring, an aromatic condensed ring or a heterocyclic condensed ring. In that case, illustrative examples of such condensed rings include the same aliphatic condensed rings, aromatic condensed rings and heterocyclic condensed rings as those exemplified with respect to $L^1$ to $L^5$.

Unsubstituted or substituted naphthyl groups suitable as the substituents X and Y in the compound of the general formula (1) which is used in the present invention are naphthyl groups represented by formulae (10) to (13) having the same substituents as those for the above phenyl groups.

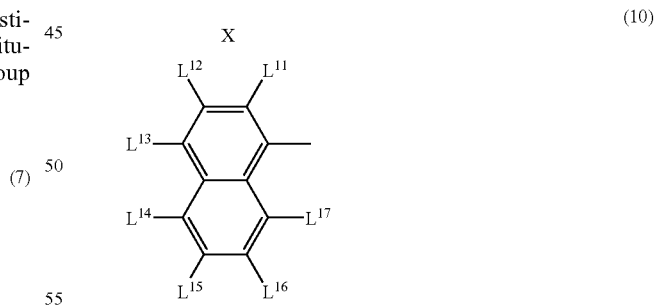
(10)

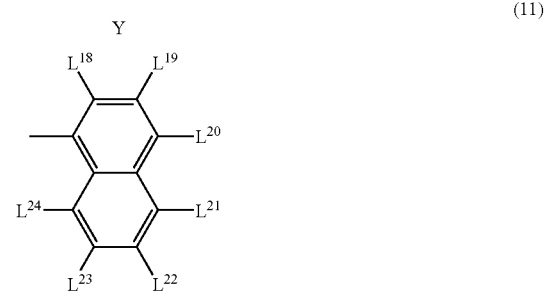
(11)

-continued (12)

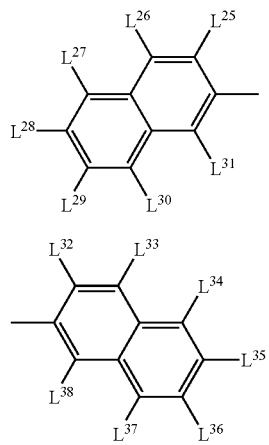

(13)

(wherein $L^{11}$ to $L^{38}$ represent the same groups as those represented by $L^1$, $L^2$, $L^3$, $L^4$ and $L^5$ in the formula (4)).

Further, $L^{11}$ to $L^{17}$, $L^{18}$ to $L^{24}$, $L^{25}$ to $L^{31}$ and $L^{32}$ to $L^{38}$ may be joined to adjacent substituents via linking groups to form an aliphatic condensed ring, an aromatic condensed ring or a heterocyclic condensed ring. In that case, illustrative examples of such condensed rings include the same aliphatic condensed rings, aromatic condensed rings and heterocyclic condensed rings as those exemplified with respect to $L^1$ to $L^5$.

Illustrative examples of substituted or unsubstituted heteroaryl groups as the substituents X and Y in the general formula (1) include heteroaryl groups having the same substituents as those enumerated for the heterocyclic ring groups. Preferable examples thereof include unsubstituted heteroaryl groups such as furanyl group, pyrrolyl group, 3-pyrrolino group, pyrazolyl group, imidazolyl group, oxazolyl group, thiazolyl group, 1,2,3-oxadiazolyl group, 1,2,3-triazolyl group, 1,2,4-triazolyl group, 1,3,4-thiadiazolyl group, pyridinyl group, pyridazinyl group, pyrimidinyl group, pyrazinyl group, triazinyl group, benzofuranyl group, indolyl group, thionaphthenyl group, benzimidazolyl group, benzothiazolyl group, benzotriazole-2-yl group, benzotriazole-1-yl group, purinyl group, quinolinyl group, isoquinolinyl group, coumarinyl group, cinnolinyl group, quinoxalinyl group, dibenzofuranyl group, carbazolyl group, phenanthronilyl group, phenothiadinyl group, flavonyl group, phthalimide group and naphthylimide group; and heteroaryl groups having the same substituents as those for the aforementioned preferable heterocyclic rings.

Further, illustrative examples of groups represented by $Q^1$ and $Q^2$ in the general formula (1) include a hydrogen atom and the same halogen atoms and substituted or unsubstituted alkyl groups as the halogen atoms and alkyl groups to be substituted into the aryl and heteroaryl groups represented by the substituents X and Y in the general formula (1).

Specific examples of skeletons of a condensed ring represented by the general formula (1) and obtained by condensation of rings A and B and a benzene ring include those represented by the following formulae (14) to (19):

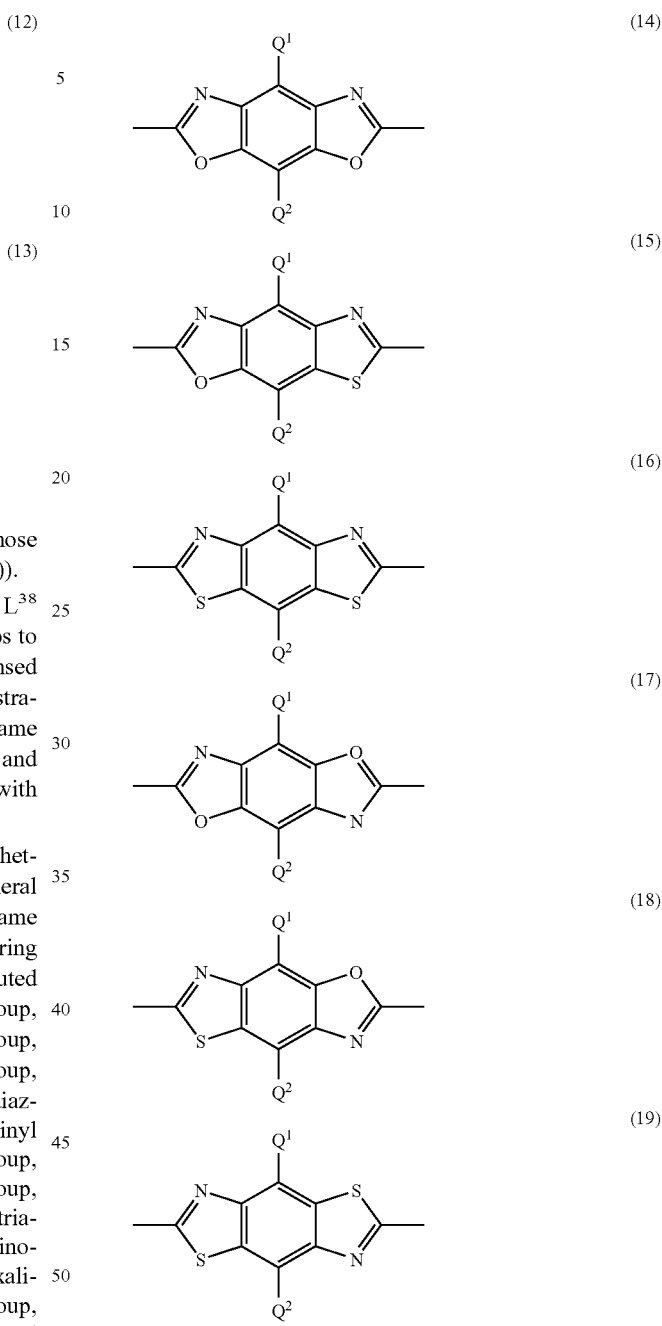

(wherein $Q^1$s and $Q^2$s represent the same groups as those represented by $Q^1$ and $Q^2$ in the formula (1)).

Particularly, as the compound of the general formula (1), a compound represented by the following general formula (2) or (3) is preferred.

(2)

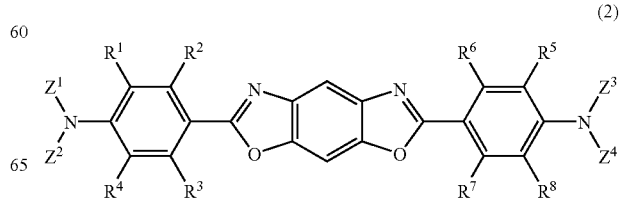

(wherein $R^1$, $R^2$, $R^3$, $R^4$, $R^5$, $R^6$, $R^7$ and $R^8$ each independently represent a hydrogen atom, a halogen atom, a hydroxyl group, a cyano group, an amino group or a substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl or acyloxy group; $Z^1$, $Z^2$, $Z^3$ and $Z^4$ each independently represent a hydrogen atom or a substituted or unsubstituted alkyl, aralkyl, aryl or alkenyl group; and substituents $R^1$ to $R^8$ and $Z^1$ to $Z^4$ may be joined to adjacent substituents via linking groups to form a ring).

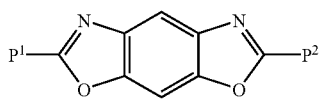

(3)

(wherein $P^1$ and $P^2$ each independently represent a substituted or unsubstituted naphthyl group, with the proviso that, in the case of a substituted naphthyl group, a substituent is selected from the group consisting of a halogen atom, a hydroxyl group, an amino group and substituted or unsubstituted alkyl, alkoxy, aralkyloxy, aryloxy, alkenyloxy, alkylthio, aralkylthio, arylthio, alkenylthio, mono-substituted amino, di-substituted amino and acyloxy groups).

In addition, in the present invention, compounds represented by formulae (1a) to (3a) which are variations of these general formulae (1) to (3) are novel compounds and are also included within a scope of the present invention.

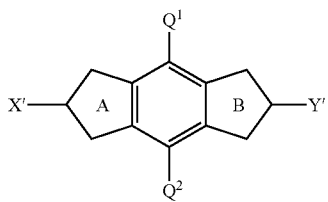

(1a)

(wherein substituents X' and Y' each independently represent an aryl or heteroaryl group, and rings A and B and $Q^1$ and $Q^2$ are the same as the rings A and B and $Q^1$ and $Q^2$ in the formula (1), with the proviso that aryl or heteroaryl groups represented by the substituents X' and Y' each independently are substituted by a substituent selected from the same halogen atoms, hydroxyl group, cyano group, amino group and substituted or unsubstituted alkyl, aralkyl, aryl, alkenyl, alkoxy, aralkyloxy, aryloxy, alkenyloxy, alkylthio, aralkylthio, arylthio, alkenylthio, mono-substituted amino, di-substituted amino, acyl, alkoxycarbonyl, aralkyloxycarbonyl, aryloxycarbonyl, alkenyloxycarbonyl, mono-substituted aminocarbonyl, di-substituted aminocarbonyl, acyloxy and heterocyclic ring groups as those described with respect to the substituents X and Y in the formula (1), and at least one substituent represents a di-substituted amino group having three or more carbon atoms or an alkoxy group having 1 to 3 oxygen atoms in a carbon chain).

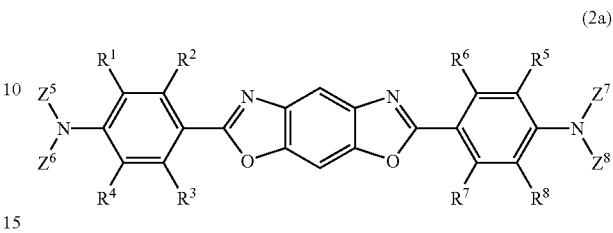

(2a)

(wherein $R^1$, $R^2$, $R^3$, $R^4$, $R^5$, $R^6$, $R^7$ and $R^8$ are the same as $R^1$, $R^2$, $R^3$, $R^4$, $R^5$, $R^6$, $R^7$ and $R^8$ in the formula (2), and $Z^5$, $Z^6$, $Z^7$ and $Z^8$ each independently represent a substituted or unsubstituted alkyl, aralkyl, aryl or alkenyl group. However, at least one of the substituents $Z^5$ to $Z^8$ represents an alkyl group having 4 to 10 carbon atoms or an aralkyl group having 7 to 10 carbon atoms).

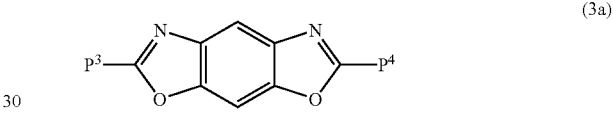

(3a)

(wherein $P^3$ and $P^4$ each independently represent a substituted or unsubstituted naphthyl group, with the proviso that, in the case of a substituted naphthyl group, a substituent is selected from the group consisting of a halogen atom, a hydroxyl group, an amino group and substituted or unsubstituted alkyl, alkoxy, aralkyloxy, aryloxy, alkenyloxy, alkylthio, aralkylthio, arylthio, alkenylthio, mono-substituted amino, di-substituted amino and acyloxy groups; at least one of $P^3$ and $P^4$ is a substituted naphthyl group; and at least one of the substituents represents an alkoxy group having 1 to 3 oxygen atoms in a carbon chain).

The compound of the general formula (1) which is used in the present invention can be synthesized by, for example, methods described in German Patent Publication DE3442293, Japanese Patent Publication Nos. 116579/1999 and 301224/1988, Macromolecules 14, 909 (1981) and Macromolecules 14, 915 (1981) or methods described in a number of literatures other than the above literatures which are known to those who have ordinary knowledge belonging to the art. As a specific example of such synthesis methods, the compound of the general formula (1) can be obtained with ease by reacting a carboxylic acid(s) represented by a formula (20) and/or a formula (21):

X—COOH (20)

Y—COOH (21)

(wherein X and Y are the same as defined above) with 2,5-diaminohydroquinone and/or hydrochloride or sulfate thereof, 2,5-diaminophenylene-4-hydroxy-1-thiol and/or hydrochloride or sulfate thereof, 2,5-diaminohydroquinone-1,4-dithiol and/or hydrochloride or sulfate thereof, 4,6- diaminoresorcinol and/or hydrochloride or sulfate thereof, 4,6-diaminophenylene-3-hydroxy-1-thiol and/or hydrochloride or sulfate thereof or 4,6-diaminophenylene-1,3-dithiol and/or hydrochloride or sulfate thereof in/without a solvent in the presence of an acid(s) such as a polyphosphoric acid and/or phosphorus pentoxide, boric acid or thionyl chloride.

Further, a compound (corresponding to the general formula (1) of the present invention) represented by a formula (25) can be obtained easily by reacting an aldehyde(s) represented by a formula (22) and/or a formula (23):

X—CHO (22)

Y—CHO (23)

(wherein X and Y are the same as defined above) with a quinone compound represented by a formula (24) in an alcohol solvent such as ethanol or propanol using a catalytic amount of a basic compound such as piperidine.

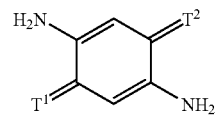

(24)

(wherein $T^1$ and $T^2$ represent an oxygen atom or a sulfur atom)

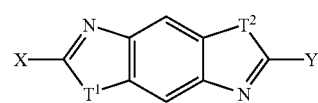

(25)

(wherein X, Y, $T^1$ and $T^2$ are the same as defined above).

Specific examples of the compound represented by the general formula (1) include compounds having structures of compounds (1-1) to (1-34) shown in Table 1.

TABLE 1

| Compound | Structural Formula |
|---|---|
| 1-1 | |
| 1-2 | |
| 1-3 | |

TABLE 1-continued
| Compound | Structural Formula |
|---|---|
| 1-4 | 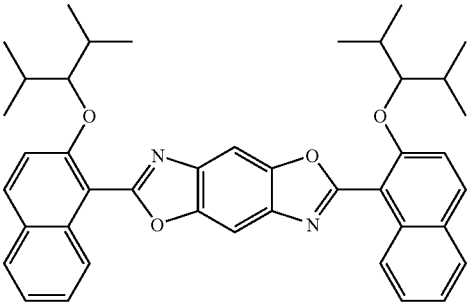 |
| 1-5 | 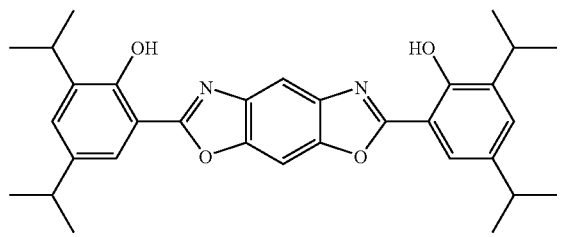 |
| 1-6 | 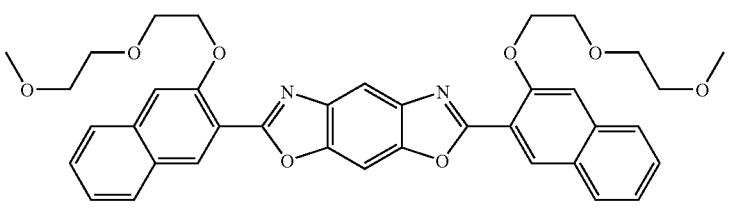 |
| 1-7 | 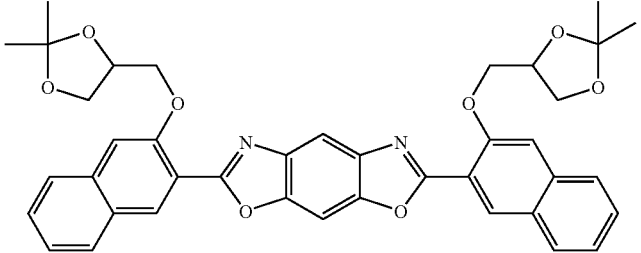 |
| 1-8 | 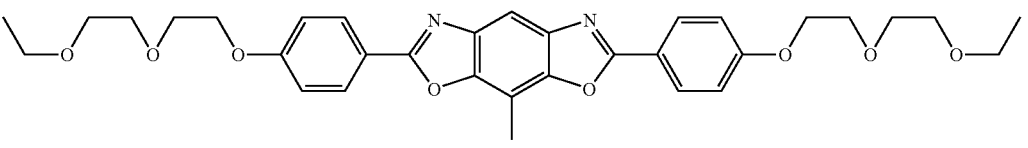 |
| 1-9 | 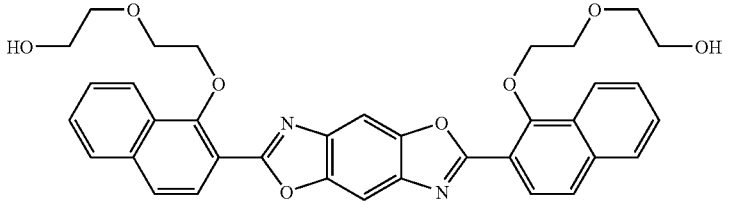 |
| 1-10 | 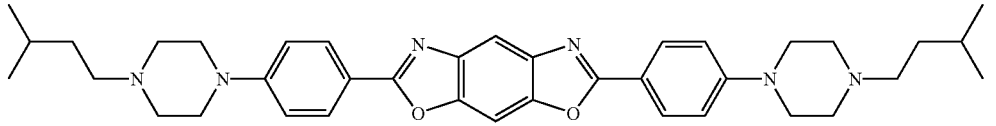 |

TABLE 1-continued
| Compound | Structural Formula |
|---|---|
| 1-11 | 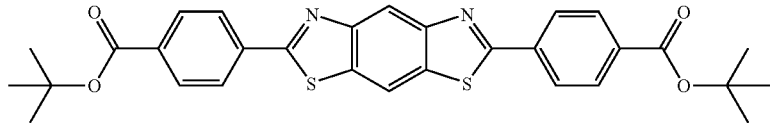 |
| 1-12 | 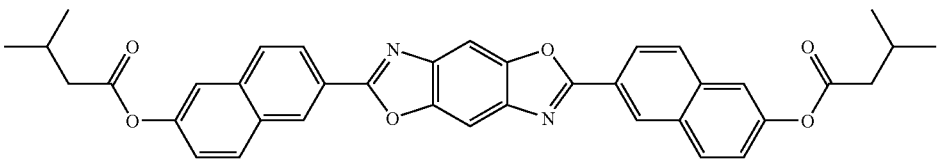 |
| 1-13 | 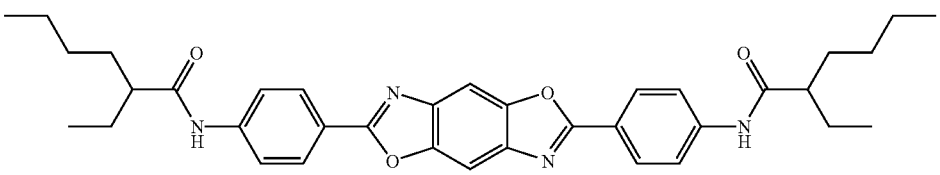 |
| 1-14 | 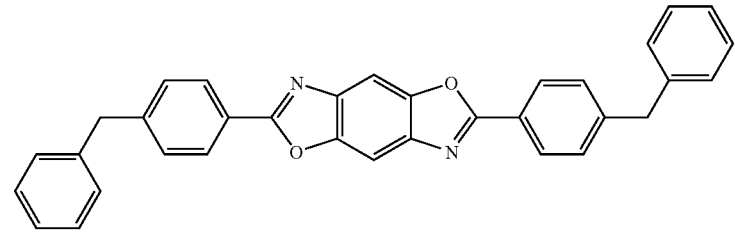 |
| 1-15 | 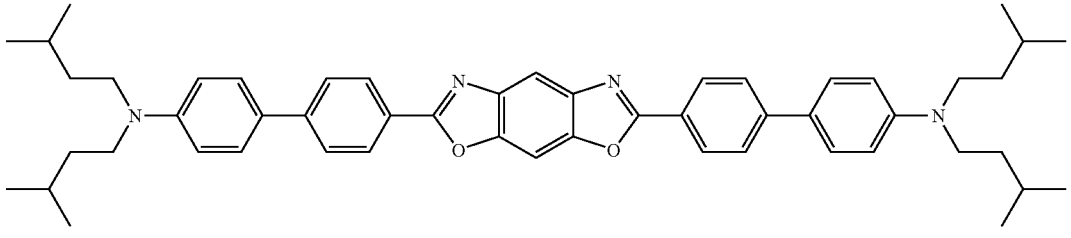 |
| 1-16 | 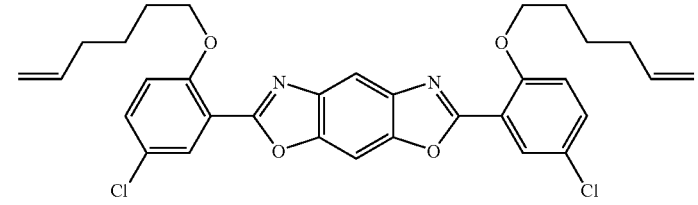 |
| 1-17 | 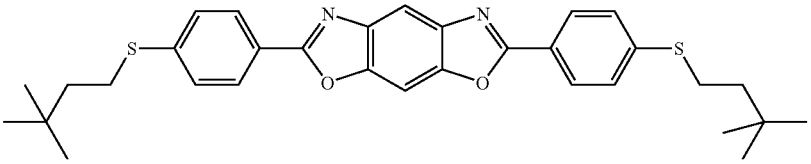 |
| 1-18 | 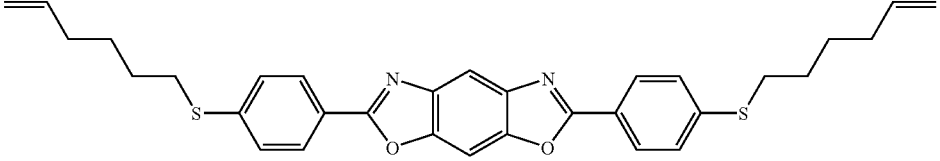 |

TABLE 1-continued

| Compound | Structural Formula |
|---|---|
| 1-19 | |
| 1-20 | |
| 1-21 | |
| 1-22 | |
| 1-23 | |
| 1-24 | |
| 1-25 | |
| 1-26 | |

TABLE 1-continued

| Compound | Structural Formula |
|---|---|
| 1-27 | |
| 1-28 | |
| 1-29 | |
| 1-30 | |
| 1-31 | |
| 1-32 | |
| 1-33 | |
| 1-34 | |

TABLE 1-continued

| Compound | Structural Formula |
|---|---|
| 1-35 | |
| 1-36 | |

A dye in a recording layer constituting the optical recording medium of the present invention comprises substantially one or more of compounds of the formula (1). Further, the dye may be mixed with a compound other than the above compounds which has an absorption maximum at wavelengths of 290 to 690 nm and a high refractive index at wavelengths of 300 to 700 nm as required. Specific examples of such a compound include a cyanine-based compound, a squarylium-based compound, a naphthoquinone-based compound, an anthraquinone-based compound, a tetrapyrazinoporphyrazine-based compound, an indophenol-based compound, a pyrylium-based compound, a thiopyrylium-based compound, an azulenium-based compound, a triphenylmethane-based compound, a xanthene-based compound, an indanthrene-based compound, an indigo-based compound, a thioindigo-based compound, a metrocyanine-based compound, a thiazine-based compound, an acridine-based compound, an oxazine-based compound, a dipyrromethene-based compound and a mixture thereof. These compounds are mixed in an amount of about 0.1 to 30% by weight.

In forming the recording layer, an additive such as a quencher, a compound thermal decomposition accelerator, an ultraviolet absorber, an adhesive, an endothermic or endothermically decomposable compound or a polymer capable of improving solubility may be mixed into the recording layer as required.

As specific examples of the quencher, metal complexes such as an acetylacetonato metal complex, a bisdithiol metal complex, e.g., a bisdithio-α-diketone metal complex and a bisphenyldithiol metal complex, a thiocatechonal metal complex, a salicylaldehydeoxime metal complex and a thiobisphenolate metal complex are preferred. In addition, an amine metal complex is also suitable.

The compound thermal decomposition accelerator is not particularly limited as long as its acceleration of thermal decomposition of a compound can be confirmed by thermal reduction analysis (TG analysis). Illustrative examples of the compound thermal decomposition accelerator include metal compounds such as a metallic antiknock agent, a metallocene compound and an acetylacetonato metal complex. Illustrative examples of the metallic antiknock agent include tetraethyllead, other lead compounds and manganese compounds such as simanthrene [$Mn(C_5H_5)(CO)_3$]. Illustrative examples of the metallocene compound include an iron biscyclopentadienyl complex (ferrocene) and biscyclopentadienyl complexes of Ti, V, Mn, Cr, Co, Ni, Mo, Ru, Rh, Zr, Lu, Ta, W, Os, Ir, Sc and Y. Of these, ferrocene, ruthenocene, osmocene, nickelocene, titanocene and derivatives thereof have a good thermal decomposition accelerating effect.

In addition to metallocenes, illustrative examples of iron-based metal compounds include organic acid iron compounds such as iron formate, iron oxalate, iron laurate, iron naphthenate, iron stearate and iron acetate; chelate iron complexes such as acetylacetonato iron complex, phenanthroline iron complex, bispyridine iron complex, ethylenediamine iron complex, ethylenediamine iron tetraacetate complex, diethylenetriamine iron complex, diethylene glycol dimethyl ether iron complex, diphosphino iron complex and dimethyl glyoximate iron complex; iron complexes such as carbonyl iron complex, cyano iron complex and ammine iron complex; iron halides such as ferrous chloride, ferric chloride, ferrous bromide and ferric bromide; inorganic iron salts such as iron nitrates and iron sulfates; and iron oxides. A thermal decomposition accelerator used in the present invention is desirably one which is soluble in an organic solvent and has good moisture and heat resistance and light resistance.

The aforementioned quenchers and compound thermal decomposition accelerators may be used alone or in admixture of two or more as required.

Illustrative examples of the endothermic or endothermically decomposable compound include compounds described in Japanese Patent Application Laid-Open No. 291366/1998 and compounds having substituents described in the publication.

Alternatively, compounds having a quenching ability, a compound thermal decomposition accelerating ability, a ultraviolet absorbing ability, an adhering ability or an endothermic or endothermically decomposing ability or polymer residues may be introduced as substitutes for compounds represented by the formula (1) as required.

In other words, a residue of a compound having a quenching ability, a compound thermal decomposition accelerating ability, a ultraviolet absorbing ability, an adhering ability or an endothermic or endothermically decomposing ability may be chemically bonded to a residue of a benzobisazole-based compound of the formula (1) set forth in the present specification via at least one single bond, double bond or triple bond to form a molecule. Preferably, each substituent of the benzobisazole-based compound of the formula (1) is a substituent represented by a formula (26).

-(L″)-(J″)  (26)

(wherein L″ represents a connection to the benzobisazole-based compound of the formula (1), that is, a single bond or an atom chain comprising 1 to 20 atoms connected by selecting at least one from a methylene, methine, amino or imino group which may be substituted, an oxygen atom or a sulfur atom; and J″ represents a compound residue having a quenching ability, a compound thermal decomposition accelerating ability, a ultraviolet absorbing ability, an adhering ability or an endothermic or endothermically decomposing ability).

Preferable examples of the atom chain represented by L″ include
a single bond,
—C(=O)—OCH$_2$—,
—C(=O)—OCH(CH$_3$)—,
—OCH$_2$—, —OCH(CH$_3$)—,
—CH$_2$OCH$_2$—,
—CH$_2$OCH(CH$_3$)—,
—CH(CH$_3$)OCH(CH$_3$)—,
—O—C(=O)—,
—CH=CH—,
—CH=N—,
—C(=O)—,
—CH=CH—C(=O)O— and
—C(C=O)CH$_2$CH$_2$C(=O)O—.

Preferable examples of J″ include metallocene residues such as a ferrocene residue, a cobaltocene residue, a nickelocene residue, a ruthenocene residue, an osmocene residue and a titanocene residue.

Suitable examples of a skeleton of the substituent of the formula (26) include the following metal complex residues:

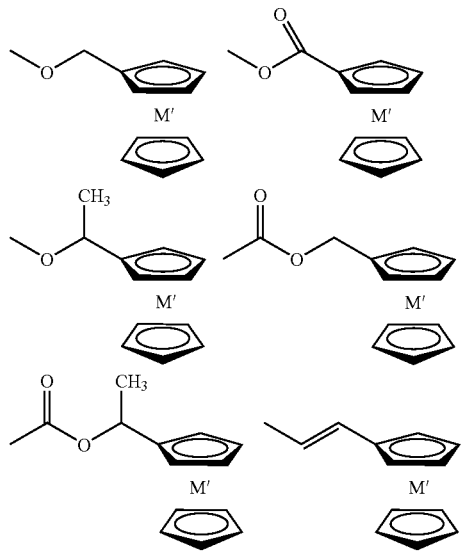

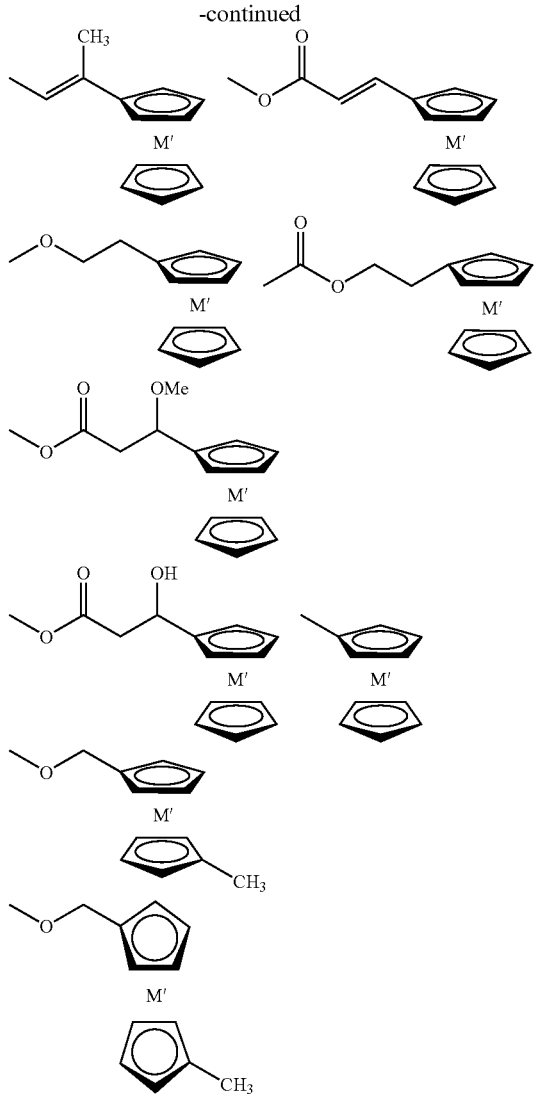

(M′ represents Fe, Ru, Co, Ni, Os or M″Z′$_2$ (wherein M″ represents Ti, Zr, Hf, Nb, Mo or V, and Z′ represents CO, F, Cl, Br, I or an alkyl, alkoxy, aryl, aryloxy, aralkyl or aralkyloxy group having 1 to 10 carbon atoms and the same substituents as the alkyl, alkoxy, aryl, aryloxy and aralkyloxy groups exemplified as the substituents for X and Y in the above formula (1)).

In addition, additives such as a binder, a leveling agent and an antifoaming agent may also be added as required. Preferable examples of the binder include polyvinyl alcohols, polyvinyl pyrrolidones, nitrocelluloses, cellulose acetates, ketone resins, acrylic resins, polystyrene resins, urethane resins, polyvinyl butyrals, polycarbonates and polyolefins.

In forming the recording layer on a substrate, a layer composed of an inorganic or polymer may be formed on the substrate so as to improve solvent resistance of the substrate, reflectivity and recording sensitivity.

As the content of the compound represented by the general formula (1) in the recording layer, any content which makes recording and reproduction possible can be selected. However, the content is generally not lower than 30% by weight, preferably not lower than 60% by weight. Further, it is also preferred that the content be substantially 100% by weight.

Illustrative examples of a method for forming the recording layer include coating methods such as spin coating, spray coating, cast coating, slide coating, curtain coating, extrusion coating, wire coating, gravure coating, spread coating, roller coating, knife coating and immersion coating, sputtering, chemical vapor deposition and vacuum deposition. Spin coating is preferred because it is easy to use.

When a coating method such as spin coating is used, a coating solution obtained by dissolving or dispersing the compound represented by the general formula (1) in a solvent such that its content would be 1 to 40% by weight, preferably 3 to 30% by weight. In this case, a solvent which causes no damage on the substrate is preferably selected as the solvent. Illustrative examples of such a solvent include alcohol solvents such as methanol, ethanol, isopropyl alcohol, octafluoropentanol, allylalcohol, methyl cellosolve, ethyl cellosolve and tetrafluoropropanol; aliphatic or alicyclic hydrocarbon solvents such as hexane, heptane, octane, decane, cyclohexane, methylcyclohexane, ethylcyclohexane and dimethylcyclohexane; aromatic hydrocarbon solvents such as toluene, xylene and benzene; halogenated hydrocarbon solvents such as carbon tetrachloride, chloroform, tetrachloroethane and dibromoethane; ether solvents such as diethyl ether, dibutyl ether, diisopropyl ether and dioxane; ketone solvents such as acetone and 3-hydroxy-3-methyl-2-butanone; ester solvents such as ethyl acetate and methyl lactate; and water. These may be used alone or in admixture of two or more.

In addition, as required, the compound in the recording layer can be dispersed in a thin polymer film or the like and used.

Further, when a solvent which causes no damage on the substrate cannot be selected, sputtering, chemical vapor deposition and vacuum deposition are effective.

The film thickness of the recording layer is 30 to 1,000 nm, preferably 50 to 300 nm. When the film thickness of the recording layer is smaller than 30 nm, recording may become impossible due to a great degree of thermal diffusion, distortion may occur in a recording signal, and amplitude of the signal may also become small. On the other hand, when the film thickness is larger than 1,000 nm, reflectivity may lower, thereby degrading reproduction signal properties.

Then, on the recording layer, a reflective layer having a thickness of preferably 50 to 300 nm is formed. To enhance reflectivity and improve adhesion, a reflection amplifying layer or an adhesion layer may be formed between the recording layer and the reflective layer. As a material of the reflective layer, one which exhibits sufficiently high reflectivity at a wavelength of reproducing light, for example, metals such as Al, Ag, Ni and Pt can be used alone or as an alloy. Of these, Ag and Al are suitable as a material of the reflective layer due to their high reflectivity. In addition to these metals, the following materials, i.e., metals and metaloids such as Mg, Se, Hf, V, Nb, Ru, W, Mn, Re, Fe, Co, Rh, Ir, Zn, Cd, Ga, In, Si, Ge, Te, Pb, Po, Sn, Bi, Au, Cu, Ti, Cr, Pd and Ta may also be contained in the reflective layer as required. Materials that make it possible to easily obtain a reflective layer composed essentially of Ag or Al and having high reflectivity are suitable. A multilayer film may be formed by laminating a thin non-metal film having a low refractive index and a thin non-metal film having a high refractive index alternately and used as the reflective layer.

Illustrative examples of a method for forming the reflective layer include sputtering, ion plating, chemical vapor deposition and vacuum deposition. Further, on the substrate or under the reflective layer, a known inorganic or organic intermediate layer or adhesion layer may be formed to improve reflectivity, recording properties and adhesion.

Further, a material of a protective layer to be formed on the reflective layer is not particularly limited as long as the material protects the reflective layer from an external force. Illustrative examples of an inorganic material include $SiO_2$, $Si_3N_4$, $MgF_2$, AlN and $SnO_2$. Meanwhile, illustrative examples of an organic material include a thermoplastic resin, a thermosetting resin, an electron beam curable resin and an ultraviolet curable resin. As for the thermoplastic resin and the thermosetting resin, the protective layer can be formed by dissolving them in an appropriate solvent to prepare a coating solution and applying and drying the coating solution. As for the ultraviolet curable resin, the protective layer can be formed by irradiating the ultraviolet curable resin with ultraviolet radiation to cure it or by first dissolving the ultraviolet curable resin in an appropriate solvent to prepare a coating solution, applying the coating solution and then irradiating the applied coating solution with ultraviolet radiation to cure it. As the ultraviolet curable resin, an acrylate resin such as urethane acrylate, epoxy acrylate or polyester acrylate can be used. These materials may be used alone or in admixture of two or more and may be formed into a multilayer film as well as a single layer.

As a method for forming the protective layer, a coating method such as spin coating or cast coating or a method such as sputtering or chemical vapor deposition is used, as in the case of the recording layer. Of these, spin coating is preferred.

The thickness of the protective layer is generally 0.1 to 100 μm. In the present invention, it is 3 to 30 μm, more preferably 5 to 20 μm.

Further, a label or the like may be printed on the protective layer.

In addition, means for laminating a protective sheet or a substrate onto the surface of the reflective layer or means for laminating one optical recording medium to the other optical recording medium such that the surfaces of reflective layers are opposed to each other may be used.

A mirror surface of the substrate may be coated with an ultraviolet curable resin, thin inorganic film or the like so as to protect the surface and to prevent dust from sticking to the surface.

Further, in a case where an optical recording medium as shown in FIG. 3 is to be prepared, a reflective layer having a thickness of preferably 1 to 300 nm is formed on a substrate. To enhance reflectivity and improve adhesion, a reflection amplifying layer or an adhesion layer may be formed between a recording layer and a reflective layer. As a material of the reflective layer, one which exhibits sufficiently high reflectivity at a wavelength of reproducing light, for example, metals such as Al, Ag, Ni and Pt can be used alone or as an alloy of these, Ag and Al are suitable as a material of the reflective layer due to their high reflectivity. In addition to these metals, the following materials, i.e., metals and metaloids such as Mg, Se, Hf, V, Nb, Ru, W, Mn, Re, Fe, Co, Rh, Ir, Zn, Cd, Ga, In, Si, Ge, Te, Pb, Po, Sn, Bi, Au, Cu, Ti, Cr, Pd and Ta may also be contained in the reflective layer as required. Materials that make it possible to easily obtain a reflective layer composed essentially of Ag or Al and having high reflectivity are suitable. A multilayer film may be formed by laminating a thin non-metal film having a low refractive index and a thin non-metal film having a high refractive index alternately and used as the reflective layer.

Illustrative examples of a method for forming the reflective layer include sputtering, ion plating, chemical vapor deposition and vacuum deposition. Further, on the substrate or under the reflective layer, a known inorganic or organic intermediate layer or adhesion layer may be formed to improve reflectivity, recording properties and adhesion.

Then, in forming the recording layer on the reflective layer, a layer composed of an inorganic or polymer may be formed on the reflective layer so as to improve solvent resistance of the reflective layer, reflectivity and recording sensitivity.

As the content of the compound represented by the general formula (1) in the recording layer, any content which makes recording and reproduction possible can be selected. However, the content is generally not lower than 30% by weight, preferably not lower than 60% by weight. Further, it is also preferred that the content be substantially 100% by weight.

Illustrative examples of a method for forming the recording layer include coating methods such as spin coating, spray coating, cast coating, slide coating, curtain coating, extrusion coating, wire coating, gravure coating, spread coating, roller coating, knife coating and immersion coating, sputtering, chemical vapor deposition and vacuum deposition. Spin coating is preferred because it is easy to use.

When a coating method such as spin coating is used, a coating solution obtained by dissolving or dispersing the compound represented by the general formula (1) in a solvent such that its content would be 1 to 40% by weight, preferably 3 to 30% by weight. In this case, a solvent which causes no damage on the reflective layer is preferably selected as the solvent. Illustrative examples of such a solvent include alcohol solvents such as methanol, ethanol, isopropyl alcohol, octafluoropentanol, allylalcohol, methyl cellosolve, ethyl cellosolve and tetrafluoropropanol; aliphatic or alicyclic hydrocarbon solvents such as hexane, heptane, octane, decane, cyclohexane, methylcyclohexane, ethylcyclohexane and dimethylcyclohexane; aromatic hydrocarbon solvents such as toluene, xylene and benzene; halogenated hydrocarbon solvents such as carbon tetrachloride, chloroform, tetrachloroethane and dibromoethane; ether solvents such as diethyl ether, dibutyl ether, diisopropyl ether and dioxane; ketone solvents such as acetone and 3-hydroxy-3-methyl-2-butanone; ester solvents such as ethyl acetate and methyl lactate; and water. These may be used alone or in admixture of two or more.

In addition, as required, the compound in the recording layer can be dispersed in a thin polymer film or the like and used.

Meanwhile, when a solvent which causes no damage on the reflective layer cannot be selected, sputtering, chemical vapor deposition and vacuum deposition are effective.

The film thickness of the recording layer is generally 1 to 1,000 nm, preferably 5 to 300 nm. When the film thickness of the recording layer is smaller than 1 nm, recording may become impossible or distortion may occur in a recording signal and amplitude of the signal may also become small. On the other hand, when the film thickness is larger than 1,000 nm, reflectivity may lower, thereby degrading reproduction signal properties.

Further, a material of a protective layer to be formed on the recording layer is not particularly limited as long as the material protects the recording layer from being adversely affected from outside by, for example, an external force or atmosphere. Illustrative examples of an inorganic material include $SiO_2$, $Si_3N_4$, $MgF_2$, AlN and $SnO_2$. Meanwhile, illustrative examples of an organic material include a thermoplastic resin, a thermosetting resin, an electron beam curable resin and an ultraviolet curable resin. As for the thermoplastic resin and the thermosetting resin, the protective layer can be formed by dissolving them in an appropriate solvent to prepare a coating solution and applying and drying the coating solution. As for the ultraviolet curable resin, the protective layer can be formed by irradiating the ultraviolet curable resin with ultraviolet radiation to cure it or by first dissolving the ultraviolet curable resin in an appropriate solvent to prepare a coating solution, applying the coating solution and then irradiating the applied coating solution with ultraviolet radiation to cure it. As the ultraviolet curable resin, an acrylate resin such as urethane acrylate, epoxy acrylate or polyester acrylate can be used. These materials may be used alone or in admixture of two or more and may be formed into a multilayer film as well as a single layer.

As a method for forming the protective layer, a coating method such as spin coating or cast coating or a method such as sputtering or chemical vapor deposition is used, as in the case of the recording layer of these, spin coating is preferred.

The film thickness of the protective layer is generally 0.01 to 1,000 µm but may be 0.1 to 100 µm or 1 to 20 µm in some cases.

In addition, means for laminating the protective sheet or the reflective layer onto the surface of the substrate or means for laminating one optical recording medium to the other optical recording medium such that the surfaces of substrates are opposed to each other may be used.

A surface of the protective layer may be coated with an ultraviolet curable resin, thin inorganic film or the like so as to protect the surface and to prevent dust from sticking to the surface.

The optical recording medium of the present invention may be housed in such a case-type protective unit for protecting a disk as seen in a floppy disk or a magneto-optical disk so as to protect the whole medium. As a material of the unit, plastic or metal such as aluminum can be used.

A laser for wavelengths of 300 to 500 nm which is used in the present invention is not particularly limited. Illustrative examples of the laser include a dye laser which can select a wavelength from a wide visible radiation range, a gas laser such as a nitrogen laser (337 nm), ion lasers such as a helium cadmium laser for a wavelength of 430, 445 or 325 nm and an argon laser for a wavelength of 457 or 488 nm, a GaN laser for a wavelength of 400 to 410 nm, an infrared laser for a wavelength of 860 nm which uses Cr-doped $LiSnAlF_6$ and generates a second harmonic of 430 nm, and a semiconductor laser such as a visible semiconductor laser for a wavelength of 415 nm, 425 nm or the like. In the present invention, an appropriate laser can be selected from the above lasers such as a semiconductor laser according to a wavelength to which a recording layer subjected to recording or reproduction of data is sensitive. High-density recording and reproduction each are possible at a wavelength or a plurality of wavelengths selected from the above semiconductor laser. A semiconductor laser is generally used for recording and reproducing data. A blue-violet semiconductor laser such as a GaN semiconductor laser for wavelengths of 400 to 410 nm is preferred.

Further, when a recording layer is formed by use of a combination of a dye sensitive to a red laser wavelength range and a dye sensitive to an infrared laser wavelength range, recording and reproduction of data based on the dyes sensitive to the red laser wavelength range and the infrared laser wavelength range may be carried out by use of a laser for a wavelength of 500 nm or higher. Specific examples of the laser include a gas laser such as a He—Ne laser and a semiconductor laser such as a visible semiconductor laser for a wavelength of 602, 612, 635, 647, 650, 660, 670 or 680 nm.

Hereinafter, examples of the present invention will be described. The present invention, however, shall not be limited in any way by these examples.

Firstly, synthesis examples of compounds associated with the present invention will be described. Measurement of parent ions by an FD-MS spectrum was made by use of "SX-102A" manufactured by JEOL, and measurement of an absorption peak (λmax) in a solution was made by use of "UV-2200" manufactured by Shimadzu Corporation.

SYNTHESIS EXAMPLE 1

Synthesis of Compound (1-1)

in Table 1:

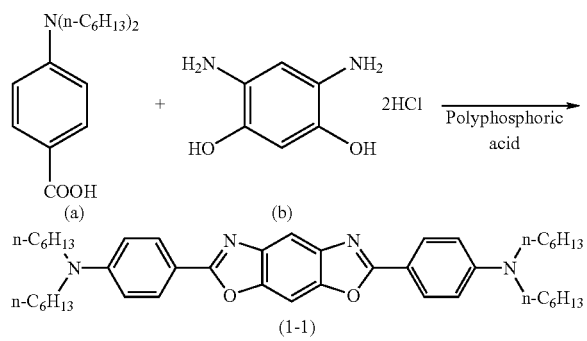

7.5 g of N,N-di(n-hexyl)aminobenzoic acid (a) and 2.6 g of 4,6-diaminoresorcinol dihydrochloride (b) were mixed into 150 g of polyphosphoric acid (manufactured by Wako Pure Chemical Industries, Ltd.), and the mixture was heated to 80° C. A hydrochloric acid gas and water vapor were deaerated as the pressure was reduced (from 26.7 kPa to 2.7 kPa), and the resulting mixture was then heated to 160° C. and caused to react for two hours. After the reaction, the mixture was cooled to 70° C., discharged into 1 kg of ice water (200 g of ice and 800 g of water), and then extracted from chloroform and then toluene. After washed with water (pH=7), an oil layer was washed with a saturated saline solution and dried over sodium sulfate. After dried, it was filtered. The filtrate was concentrated, and a main component was collected from the residue by silica gel chromatography (developer: chloroform/ethyl acetate=50/2→50/4; silica gel: 500 ml). After concentrated, it was recrystallized (at 20° C.) from a chloroform/acetone system. After filtration, the filtered mass was washed with acetone and dried at 60° C. under a reduced pressure to give 4.88 g of a compound (1-1) (benzo[2,3-d,5,6-d']bis{2-[4-(N,N-di(n-hexyl)amino)-phenyl]oxazole}).

The results of analysis of the compound (1-1) are shown in the following table:

| | [Elementary Analysis Values] | | |
|---|---|---|---|
| | Carbon (%) | Hydrogen (%) | Nitrogen (%) |
| Calculated Values | 77.83 | 9.20 | 8.25 |
| Measured Values | 78.74 | 9.24 | 8.27 |

[Absorption Spectrum]

λmax=391.6 nm (toluene)

$\varepsilon g=1.79 \times 10^5$ ml g$^{-1}$cm$^{-1}$

[FD-MS]

m/z: 678

This compound was dissolved in 1,2-dimethylcyclohexane (to be abbreviated as "DMCH" hereinafter) at a concentration of 2.2% by weight.

SYNTHESIS EXAMPLE 2

Synthesis of Compound (1-6) in Table 1

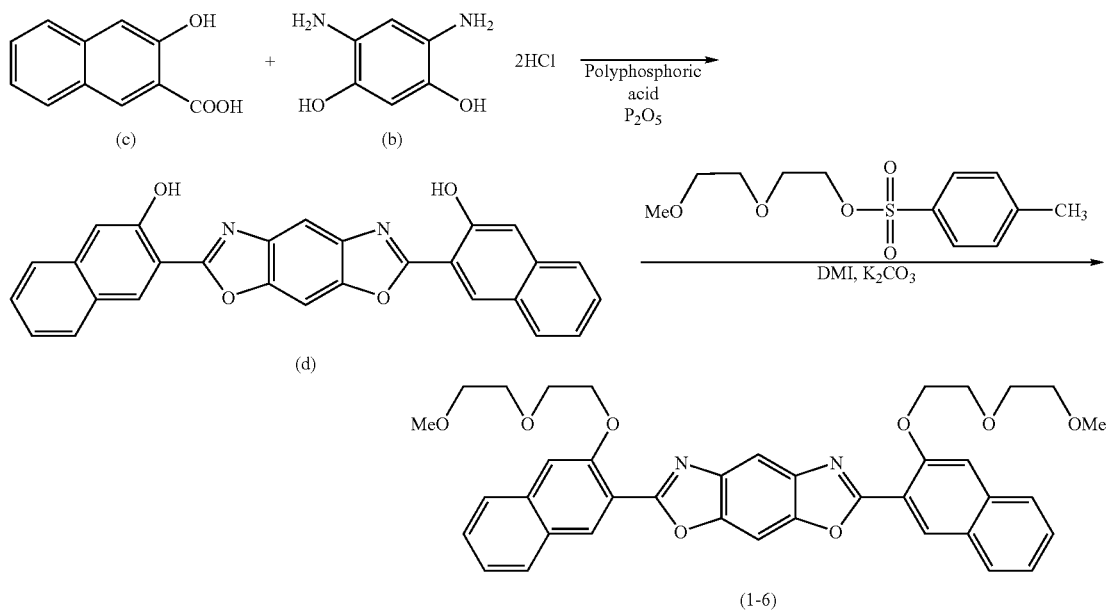

7.52 g of 2-hydroxy-3-naphthoic acid (c) and 4.9 g of 4,6-diaminoresorcinol dihydrochloride (b) were mixed into 18.8 g of polyphosphoric acid (manufactured by Wako Pure Chemical Industries, Ltd.), and the mixture was heated to 80° C. A hydrochloric acid gas and water vapor were deaerated for one hour as the pressure was reduced (from 26.7 kPa to 2.7 kPa). Then, the reduced pressure was restored to an atmospheric pressure in a nitrogen atmosphere, 13.7 g of diphosphorus pentoxide was charged into the mixture, and the resulting mixture was heated to 190° C. and caused to react for 4 hours. After the reaction, 56.4 g of phosphoric acid was added dropwise over 5 minutes. Thereafter, the resulting mixture was cooled to 80° C. A reaction mass was discharged into 500 g of ice water and stirred at room temperature for one night. The solution was neutralized (to a pH of 5 or higher) with a concentrated NaOH aqueous solution. The resulting solution was filtered, and the filtered mass was washed with water (pH=7) and then with methanol (100 ml) and then dried at 70° C. under a reduced pressure to give 8.4 g of a crude compound (d).

Then, 5.0 g of the crude compound (d), 6.15 g of 2-(2-methoxyethoxy)ethyl-p-toluenesulfonate, 30 ml of N,N-dimethylimidazolizine-2-one (to be abbreviated as "DMI" hereinafter) and 1.56 g of potassium carbonate were mixed together, and the mixture was caused to react at 200° C. for 6 hours. After cooled to room temperature, the mixture was discharged into 500 ml of water. The resulting solution was stirred for one hour and then left to stand for one night. A discharged mass was filtered, and washed with water (100 ml×5 times) until pH of the filtrate indicated that it became neutral. The filtered mass was dried at 60° C. under a reduced pressure to give 6.06 g of a crude compound (1-6).

Then, the crude compound was subjected to silica gel chromatography (first time: chloroform/acetone (developer)=100/0→9/1→8/2; silica gel: 350 ml, second time: chloroform/ethyl acetate (developer)=1/1; silica gel: 500 ml) to collect a main component. After the collected solution was concentrated, the concentrated residue was purified by recrystallization from an acetone/chloroform system and then an acetone/toluene system and dried at 60° C. under a reduced pressure to give 0.39 g of a compound (1-6) (benzo[2,3-d,5,6-d']bis{2-[3-[2-(2-methoxyethoxy)ethoxy]naphthyl]oxazole}).

The results of analysis of the compound (1-6) are shown in the following table:

| [Elementary Analysis Values] | | | |
|---|---|---|---|
| | Carbon (%) | Hydrogen (%) | Nitrogen (%) |
| Calculated Values | 70.35 | 5.59 | 4.32 |
| Measured Values | 71.03 | 5.69 | 4.37 |

[Absorption Spectrum]

$\lambda$max=345.4 nm (chloroform)

$\epsilon$g=7.6×10$^4$ ml g$^{-1}$ cm$^{-1}$

[FD-MS]

m/z: 648

This compound was dissolved in 2,2,3,3-tetrafluoropropanol at a concentration of 17% by weight.

SYNTHESIS EXAMPLE 3

Synthesis of Compound (1-36) in Table 1

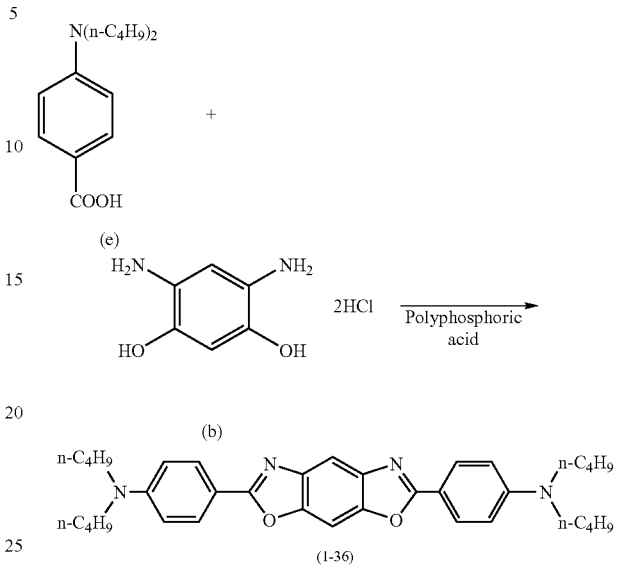

1.0 q (4.01 mmol) of N,N-dibutylaminobenzoic acid (e) and 0.62 g (2.8 mmol) of 4,6-diaminoresorcinol dihydrochloride (b) were mixed into 25 g of polyphosphoric acid (manufactured by Wako Pure Chemical Industries, Ltd.), and the mixture was heated to 80° C. A hydrochloric acid gas and water vapor were deaerated as the pressure was reduced (from 26.7 kPa to 2.7 kPa), and the resulting mixture was then heated to 160° C. and caused to react for two hours. After the reaction, the mixture was cooled to room temperature, discharged into 200 ml of water and then extracted from toluene. After washed with water (pH=7), an oil layer was washed with a saturated saline solution and dried over sodium sulfate. After dried, it was filtered. The filtrate was concentrated, and a main component was collected from the residue by silica gel chromatography (developer: chloroform/ethyl acetate=95/5; silica gel: 350 ml). After the collected solution was concentrated, it was recrystallized (at −20° C.) from a chloroform/acetone system. After filtration, the filtered mass was washed with acetone and dried at 60° C. under a reduced pressure to give 0.21 g of a compound (1-36) (benzo[2,3-d,5,6-d']bis{2-[4-(N,N-dibutylamino)phenyl]oxazole}).

The results of analysis of the compound (1-36) are shown in the following table:

| [Elementary Analysis Values] | | | |
|---|---|---|---|
| | Carbon (%) | Hydrogen (%) | Nitrogen (%) |
| Calculated Values | 76.29 | 8.18 | 9.88 |
| Measured Values | 75.21 | 8.20 | 9.64 |

[Absorption Spectrum]

$\lambda$max=391.2 nm (toluene)

$\epsilon$g=1.95×10$^5$ ml g$^{-1}$cm$^{-1}$

[FD-MS]

m/z: 566

This compound was dissolved in DMCH at a concentration of 0.9% by weight.

EXAMPLE 1

Of compounds represented by the general formula (1), a film of the compound (1-1) which had a thickness of 70 nm was formed on a disk-shaped substrate composed of a polycarbonate resin, having a continuous guide groove (track pitch: 0.74 μm) and having an external diameter of 120 mm and a thickness of 0.6 mm by a vacuum deposition method.

Then, on this recording layer, Ag was sputtered by use of a sputtering machine (CDI-900) manufactured by BALZAS to form a reflective layer having a thickness of 100 nm. An argon gas was used as a sputtering gas. Sputtering was carried out with a sputtering power of 2.5 kW at a sputtering gas pressure of 1.33 Pa ($1.0 \times 10^{-2}$ Torr).

Then, on the reflective layer, an ultraviolet curable resin SD-17 (manufactured by DAINIPPON INK AND CHEMICALS, INCORPORATED) was spin-coated. Then, a polycarbonate resin substrate similar to the above substrate but having no guide groove was placed on the coated reflective layer and then irradiated with ultraviolet radiation, thereby bonding the substrates together. Thus, an optical recording medium was prepared.

The optical recording medium having the thus formed recording layer therein was subjected to the following evaluation tests:

When a signal having a recording frequency of 9.7 MHz was recorded on the optical recording medium with a power of 8.5 mW at a linear velocity of 5.0 m/s and a shortest pit length of 0.26 μm by use of an evaluation device equipped with a blue semiconductor laser head adapted to a wavelength of 403 nm and having an N.A. of 0.65, pits were formed and the signals were recorded. When the recorded medium was replayed at a linear velocity of 5.0 m/s by use of the same evaluation device, the pits could be read. A C/N ratio was as good as 30 dB or higher.

EXAMPLES 2 TO 5

Optical recording media were prepared in the same manner as in Example 1 except that compounds (1-2) to (1-5) were used in recording layers, and signals were recorded in the same manner as in Example 1. As a result, pits were successfully formed and the signals were successfully recorded on all the optical recording media. Further, the pits could be read.

EXAMPLE 6

0.2 g of a compound (1-6) was dissolved in 10 ml of tetrafluoropropanol to prepare a compound solution.

The compound solution was spin-coated on a disk-shaped substrate composed of a polycarbonate resin, having a continuous guide groove (track pitch: 0.74 μm) and having an external diameter of 120 mm and a thickness of 0.6 mm at a rotational speed of 1,500 $min^{-1}$ and then dried at 70° C. for 2 hours to form a recording layer.

An optical recording medium was prepared in the same manner as in Example 1 except for formation of the above recording layer, and signals were recorded in the same manner as in Example 1. As a result, pits were successfully formed and the signals were successfully recorded on the optical recording medium. When the recorded medium was played at a linear velocity of 5.0 m/s by use of the same evaluation device, the pits could be read. A C/N ratio was as good as 30 dB or higher.

EXAMPLES 7 TO 30

Optical recording media were prepared in the same manner as in Example 1 except that compounds (1-7) to (1-30) were used in recording layers, and signals were recorded in the same manner as in Example 1. As a result, pits were successfully formed and the signals were successfully recorded on all the optical recording media. Further, the pits could be read.

EXAMPLE 31

An optical recording medium was prepared in the same manner as in Example 6 except that a compound (1-31) were used in a recording layer, and signals were recorded in the same manner as in Example 6. As a result, pits were successfully formed and the signals were successfully recorded on the optical recording medium. Further, the pits could be read.

EXAMPLES 32 TO 36

Optical recording media were prepared in the same manner as in Example 1 except that compounds (1-32) to (1-36) were used in recording layers, and signals were recorded in the same manner as in Example 1. As a result, pits were successfully formed and the signals were successfully recorded on all the optical recording media. Further, the pits could be read.

EXAMPLE 37

0.2 g of the compound (1-1) was dissolved in 10 ml of 1,2-dimethylcyclohexane to prepare a compound solution.

The compound solution was spin-coated on a disk-shaped substrate composed of a polycarbonate resin, having a continuous guide groove (track pitch: 0.74 μm) and having an external diameter of 120 mm and a thickness of 0.6 mm at a rotational speed of 1,500 $min^{-1}$ and dried to form a recording layer.

An optical recording medium was prepared in the same manner as in Example 1 except for formation of the above recording layer, and signals were recorded in the same manner as in Example 1. As a result, pits were successfully formed and the signals were successfully recorded on the optical recording medium. When the recorded medium was played at a linear velocity of 5.0 m/s by use of the same evaluation device, the pits could be read.

EXAMPLE 38

An optical recording medium was prepared in the same manner as in Example 37 except that compound (1-32) were used in a recording layer, and signals were recorded in the same manner as in Example 37. As a result, pits were successfully formed and the signals were successfully recorded on the optical recording medium. Further, the pits could be read.

COMPARATIVE EXAMPLE 1

An optical recording medium was prepared in the same manner as in Example 6 except that a compound of formula (f):

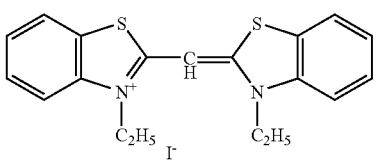

was used in place of the compound (1-6), and recording and reproduction were evaluated with respect to the optical recording medium. As a result, a C/N ratio was as low as 20 dB, and the medium was not successfully played.

As described in Examples 1 to 38, the optical recording medium of the present invention achieves recording and reproduction of data in a blue laser wavelength range and has excellent recording properties.

Thus, signals can be recorded on a recording layer containing a compound having a structure defined in the present invention by a laser beam whose wavelength is selected from a wavelength range of 300 to 500 nm, and the optical recording medium of the present invention can be used as an optical recording medium which uses a laser beam whose wavelength is selected from a wavelength range of 300 to 500 nm to record and reproduce data.

INDUSTRIAL APPLICABILITY

According to the present invention, use of a compound represented by the general formula (1) in a recording layer makes it possible to provide a recordable optical recording medium which data can be recorded on or reproduced from by use of a laser having a wavelength of 300 to 500 nm and capable of high density recording.

What is claimed is:

1. A benzobisazole-based compound represented by the following general formula (3a):

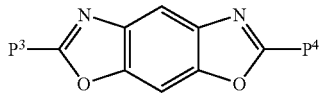

(wherein $P^3$ and $P^4$ each independently represent a substituted or unsubstituted naphthyl group, with the proviso that, in the case of a substituted naphthyl group, a substituent is selected from the group consisting of halogen atoms, a hydroxyl group, an amino group and substituted or unsubstituted alkyl, alkoxy, aralkyloxy, aryloxy, alkenyloxy, alkylthio, aralkylthio, arylthio, alkenylthio, mono-substituted amino, di-substituted amino and acyloxy groups, at least one of $P^3$ and $P^4$ is a substituted naphthyl group, and at least one of the substituents represents an alkoxy group having two to three oxygen atoms in a carbon chain).

2. An optical recording medium having a recording layer on a substrate with continuous guide grooves, and being capable of recording and reproduction by a laser light, wherein the recording layer contains at least one benzobisazole-based compound of claim 1.

3. The medium of claim 2, which makes it possible to record and reproduce data by use of a laser beam whose wavelength is selected from a wavelength range of 300 to 500 nm.

4. The medium of claim 2, which makes it possible to record and reproduce data by use of a laser beam whose wavelength is selected from a wavelength range of 400 to 500 nm.

5. The medium of claim 2, which makes it possible to record and reproduce data by use of a laser beam whose wavelength is selected from a wavelength range of 400 to 410 nm.

* * * * *